US006287871B1

(12) United States Patent
Herron et al.

(10) Patent No.: US 6,287,871 B1
(45) Date of Patent: Sep. 11, 2001

(54) SYSTEM FOR DETERMINING ANALYTE CONCENTRATION

(75) Inventors: James N. Herron; Douglas A. Christensen, both of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/142,947
(22) PCT Filed: Mar. 19, 1997
(86) PCT No.: PCT/US97/04377
  § 371 Date: Sep. 18, 1998
  § 102(e) Date: Sep. 18, 1998
(87) PCT Pub. No.: WO97/35181
  PCT Pub. Date: Sep. 25, 1997

Related U.S. Application Data
(60) Provisional application No. 60/013,684, filed on Mar. 19, 1996.

(51) Int. Cl.$^7$ .................................................. G01N 21/64
(52) U.S. Cl. ...................... 436/172; 436/532; 422/82.08; 422/82.11

(58) Field of Search .............................. 422/82.08, 82.11, 422/102; 436/532, 165, 172, 809, 527

(56) References Cited

U.S. PATENT DOCUMENTS

| Re. 33,064 | * | 9/1989 | Carter et al. ........................... 436/34 |
| 4,772,453 | * | 9/1988 | Lisenbee ................................. 422/52 |
| 5,290,513 | * | 3/1994 | Berthold et al. ........................ 422/52 |
| 5,401,465 | * | 3/1995 | Smethers et al. ...................... 422/52 |

FOREIGN PATENT DOCUMENTS

9427137  *  11/1994  (WO) .

* cited by examiner

Primary Examiner—Jeffrey Snay
(74) Attorney, Agent, or Firm—TraskBritt

(57) ABSTRACT

The present invention relates to a system (80) for determining analyte concentration. The system (80) includes an optical detection system (92) that detects fluorescence from fluorescent binding assays in a biosensor (88). A processing system (96) may be used to determine analyte concentration from the fluorescence detected by the optical detection system (92). The optical detection system (92) may include photodetectors with or without in series lenses. Alternatively, a CCD camera (146) may be used.

23 Claims, 16 Drawing Sheets

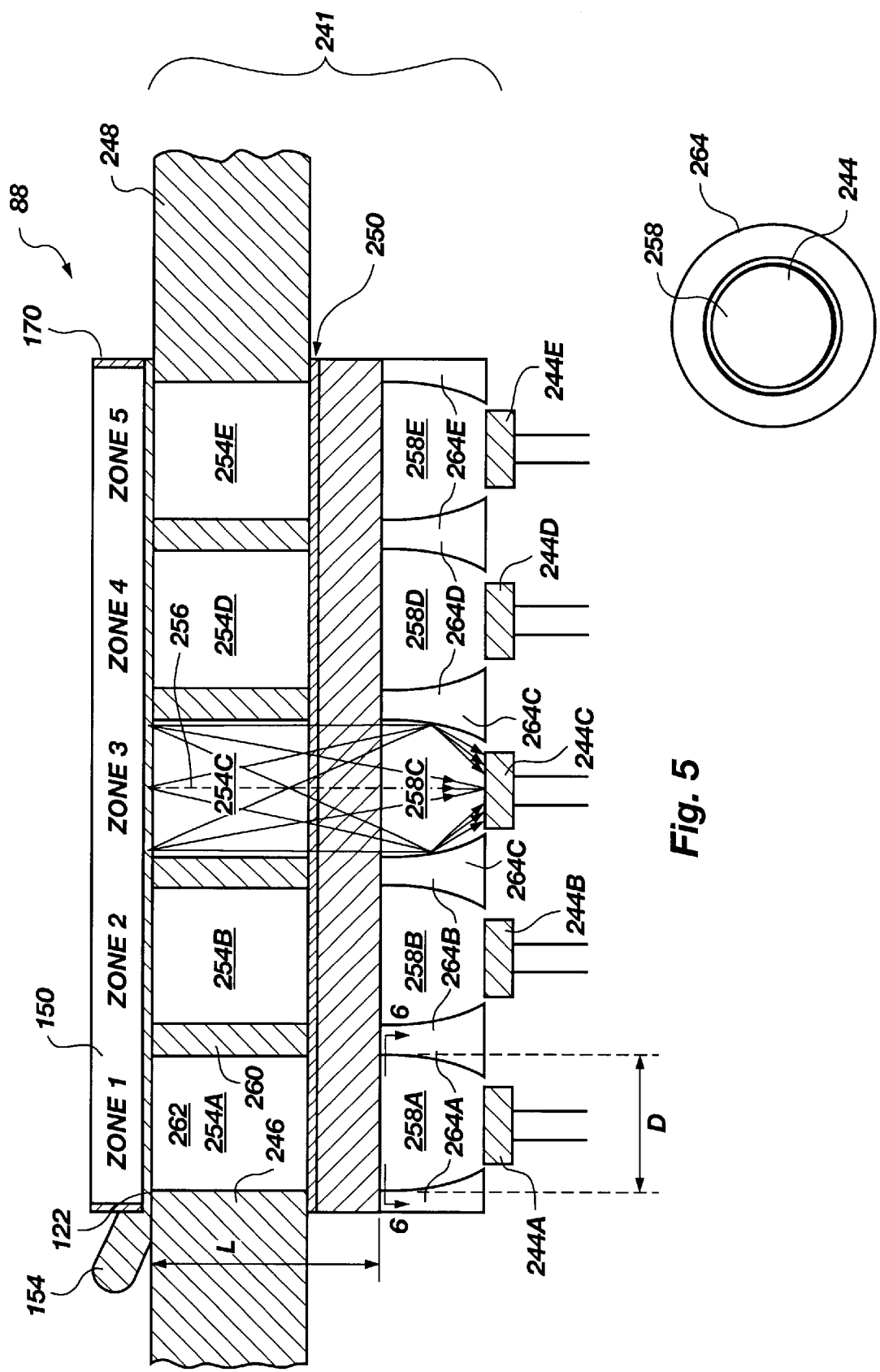

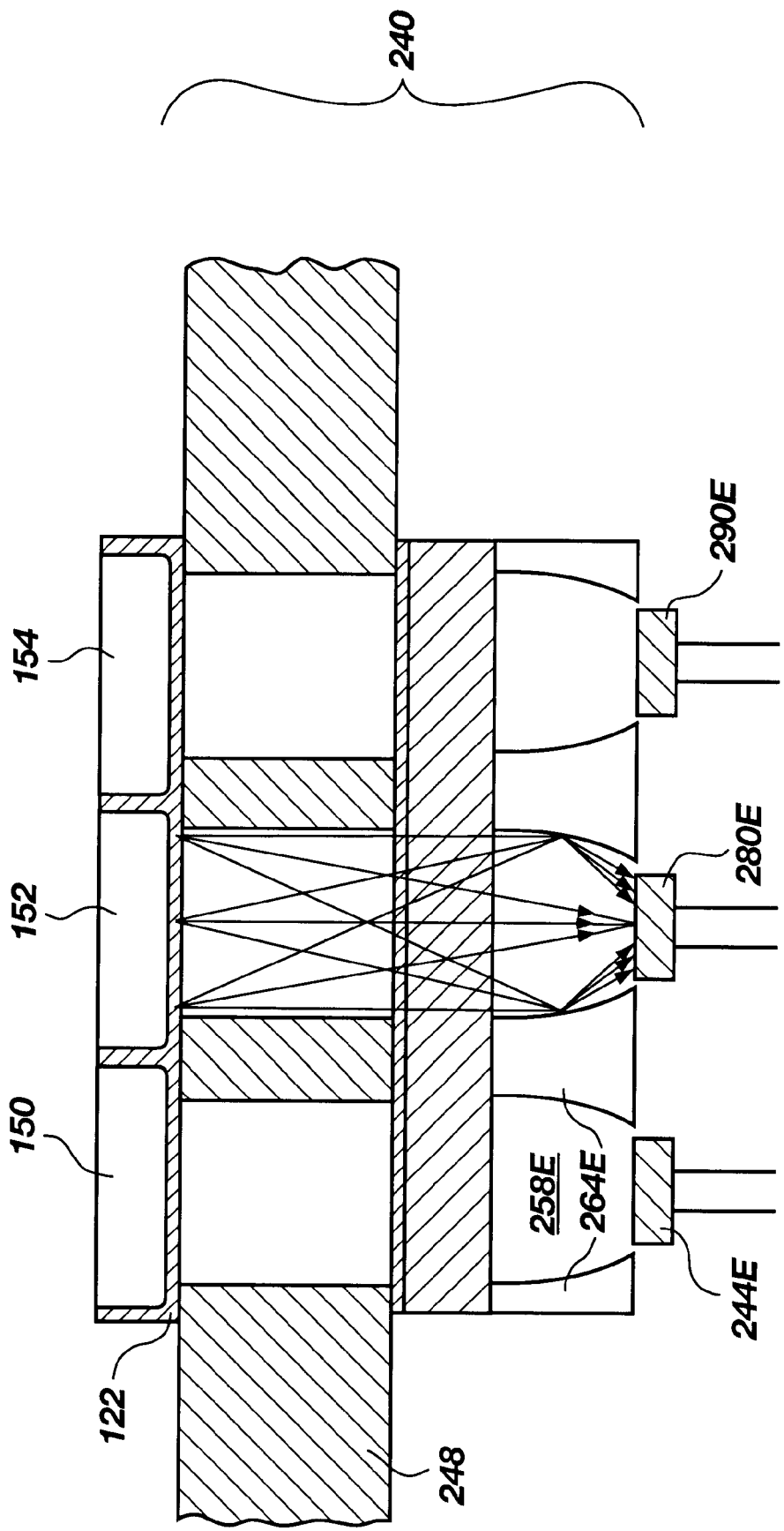

First Assay Zone ↓

Third Assay Zone ↓

← Flow Channel 3

First Assay Zone ↓

Third Assay Zone ↓

Standard Curves for CK-MB and Myoglobin Assays

SYSTEM FOR DETERMINING ANALYTE CONCENTRATION

This application is the National Stage of International Application No. PCT/US97/04377, filed Mar. 19, 1997, which claims the benefit of U.S. Provisional Application No. 60/013,684, filed Mar. 19, 1996.

TECHNICAL FIELD

This present invention relates to a system and method for determining analyte concentration including an optical detection system that detects fluorescence from fluorescent assays, and a processing system that determines analyte concentration from the fluorescence.

BACKGROUND ART

Biosensor apparatus based on optical detection of analytes by fluorescence of tracer molecules, have attracted increasing attention in recent years. Such apparatus are useful for both diagnostic and research purposes. In particular, biosensors for a solid-phase fluoroimmunoassay, in which a capture molecule such as an antibody or antibody fragment specific to the desired analyte is immobilized on a substrate, and binding of the analyte to the antibody results either directly or indirectly (for example, by means of a labelled tracer) in a fluorescence signal, are becoming an important class of optical biosensor.

In most solid-phase fluoroimmunoassays, to achieve adequate sensitivity a "wash" step is required to remove unbound tracer before measuring the fluorescence. This problem is particularly true for detection of analytes present at concentrations below nanomolar, as is the case for many analytes of interest in body fluids including blood, serum and urine. However, the wash step is tedious, and care on the part of the technician is required to produce repeatable and accurate results. Accordingly, it is highly desirable to provide a fluoroimmunoassay system in which sensitivity to analyte concentrations of $10^{-10}$ to $10^{-13}$ molar or below is achieved without a wash step.

An optical technique known as total internal reflection (abbreviated "TIR") provides one approach to such a system. Evanescent light is light produced when a light beam traveling in a waveguide is totally internally reflected at the interface between the waveguide and a surrounding medium having a lower refractive index. A portion of the electromagnetic field of the internally reflected light penetrates into the surrounding medium and constitutes the evanescent light field. The intensity of evanescent light drops off exponentially with distance from the waveguide surface. In a fluoroimmunoassay, evanescent light can be used to selectively excite tracer molecules directly or indirectly bound to an immobilized binding agent, while tracer molecules free in solution beyond the evanescent penetration distance are not excited and thus do not contribute "background" fluorescence. The use of evanescent field properties for fluorescence measurements is sometimes referred to as evanescent sensing. For a glass or a similar silica-based material, or an optical plastic such as polystyrene, with the surrounding medium being an aqueous solution, the region of effective excitation by evanescent light generally extends about 1000 to 2000 Å (angstroms) from the waveguide surface. This depth is sufficient to excite most of the tracer molecules bound to the capture molecules (antibodies, receptor molecules, and the like, or fragments thereof) on the waveguide surface, without exciting the bulk of the tracer molecules that remain free in solution. The fluorescence thus resulting reflects the amount of tracer bound to the immobilized capture molecules, and in turn the amount of analyte present.

The tracer fluorescent light will conversely also evanescently penetrate back into the waveguide and be propagated therein. The maximum solution depth for efficient evanescent collection by the waveguide approximates the depth of the region of evanescent penetration into the solution, and thus the waveguide-penetrating portion of the tracer fluorescence can also be used to selectively measure fluorescence from tracer bound to the waveguide surface.

U.S. Pat. No. RE 33,064 to Carter, U.S. Pat. No. 5,081,012 to Flanagan et al, U.S. Pat. No. 4,880,752 to Keck, U.S. Pat. No. 5,166,515 to Attridge, and U.S. Pat. No. 5,156,976 to Slovacek and Love, and EP publications Nos. 0 517 516 and 0 519 623, both by Slovacek et al, all disclose apparatus for fluoroimmunoassays utilizing evanescent sensing principles.

Desirably, an immunofluorescent biosensor should be capable of detecting analyte molecules at concentrations of $10^{-12}$ M (molar) or below. To date, most reports of evanescent-type biosensors indicate that at best, concentrations of $10^{-11}$ M could be detected.

It is further desirable for speed and convenience in "routine" testing, for example testing of blood bank samples for viral antibodies, to have an evanescent immunofluorescent biosensor which is disposable and which provides multi-sample measurement capability. Multi-sample capability would allow a test sample and a control sample (such as a blank, a positive control, or for a competition-type assay, a sample pre-loaded with tracer molecules) to be simultaneously illuminated and measured. Simultaneous multi-sample capability would also speed up the process of analyzing multiple samples and would reduce the effects of variation in the level of exciting light which are known to occur with typical light sources. However, in a typical prior art evanescent light device such as that of Block et al, U.S. Pat. No. 4,909,990 issued Mar. 20, 1990, the waveguide is a fiber optic rod whose shape makes it difficult to build a multi-well biosensor.

Another factor which affects the attainable sensitivity relates to the intensity of excitation light emitted from the waveguide. The intensity of fluorescence emitted by tracer molecules is in part dependent on the intensity of exciting light (which is the evanescent field). Therefore, increased evanescent light intensity should provide increased fluorescence which in turn would improve the detection sensitivity. The level of evanescent light is in turn dependent on the intensity of the light beam propagating in the waveguide, and this can be increased, for a given power in the excitation beam, by decreasing the cross-sectional area of the waveguide.

Previous methods of immobilizing antibodies to optical substrates in evanescent biosensors also present some problems causing reduction in sensitivity. Many such methods utilize the ε-amino groups of lysine residues in the protein. This approach has at least two significant disadvantages due to the fact that many proteins have multiple lysine residues. First, the presence of multiple potential coupling sites (multiple lysine residues) results in multiple random orientations of antibodies on the substrate surface. If the substrate-coupled lysine residue is near the N-terminal of the antibody molecule, the antibody's antigen binding site (which is near the N-terminal) may be effectively unavailable for binding of the analyte.

Second, if multiple lysines on the same antibody molecule are coupled to the substrate, the molecule may be subjected to conformational strains which distort the antigen binding site and alter its binding efficiency. For capture molecules immobilized by typical prior methods, generally only 20% or less of the binding sites are functional for analyte binding. Thus, it is desirable to have a site-specific method for coupling of the antibodies or other proteins, so that the capture molecules will be uniformly oriented and available for analyte binding.

Another problem relates to the levels of non-specific binding to the antibody-coated surface of the optical substrate. These levels are often sufficiently high to make detection of analyte at concentrations below about $10^{-10}$ M very difficult. Non-specific binding can be reduced by including a wash step after the sample is incubated with the coated substrate, to remove unbound tracer molecules. However, as previously discussed, a wash step is undesirable. Second, non-specific binding can be a serious problem unless the surface is "passivated" with a masking agent such as bovine serum albumin or with a thin coating of hydrophilic polymer such as poly(ethylene glycol) or poly (methacrylate). Without such passivation (which introduces yet another step into the procedure), non-specific binding can be 50% or more of the specific binding. Even with passivated surfaces, non-specific binding can be sufficient to reduce detection sensitivity and reproducibility.

Thus, a need remains for an evanescent biosensor system which provides the desired sensitivity in a homogeneous assay (homogeneous being defined for purposes of this application as meaning an assay that does not require a wash step). A need further remains for such an apparatus with improved sensitivity for detection of analytes at picomolar concentrations and below. A need also remains for an immunofluorescent assay and biosensor with properties of low non-specific binding and having uniformly oriented capture molecules. A need also remains for such a biosensor and assay system which are inexpensive and readily used by non-skilled persons.

DISCLOSURE OF INVENTION

The present invention discloses a method and apparatus for determining the presence and/or concentration of one or more analytes in a sample. In one embodiment of the invention, a method of simultaneously determining the presence of a plurality of analytes in a sample is disclosed. The method of determining the presence of a plurality of analytes comprises one or more of the following steps, either individually or in combination: providing a biosensor having a waveguide and a plurality of patches disposed within a well defined in the waveguide, a first patch of the plurality of patches having a first type of capture molecule associated therewith, and a second patch of the plurality of patches having a second type of capture molecule associated therewith; introducing a sample believed to contain a plurality of analytes into the well; introducing at least one type of tracer molecule into the well, the tracer molecule comprising a fluorescent label bonded to a molecule that binds with either one of the first type and the second type of capture molecules or to at least one analyte of the plurality of analytes; directing light through the waveguide, the light having a wave length which will excite the fluorescent label; isolating fluorescent light emanating from the first patch from light emanating from the second patch and light emanating from a remainder of the biosensor; isolating fluorescent light emanating from the second patch from light emanating from the first patch and light emanating from the remainder of the biosensor; detecting the fluorescent light emanating from the first patch with a first photodetector; detecting the fluorescent light emanating from the second patch with a second photodetector; analyzing the fluorescent light emanating from the first patch to determine a presence of a first analyte; and analyzing the light emanating from the second patch to determine a presence of a second analyte.

The invention furthermore discloses a method of simultaneously determining the individual concentration of several analytes in a sample, comprising one or more of the following steps, either individually or in combination: providing a biosensor having a waveguide which defines a first well and a second well and a plurality of patches disposed within the first and second wells, each the first and second wells containing a first patch of the plurality of patches having a first type of capture molecule associated therewith and a second patch of the plurality of patches having a second type of capture molecule associated therewith; introducing a sample believed to contain a first analyte and a second analyte into the first well; introducing a first liquid containing first known quantities of the first analyte and the second analyte into the second well; introducing at least one type of tracer molecule into the first well and into the second well, the tracer molecule comprising a fluorescent label bonded to a molecule that binds with either one of the first and second types of capture molecules or at least one of the first and second analytes; directing light through the waveguide, the light having a wave length which will excite the fluorescent label; isolating fluorescent light emanating from the first patch in the first well from fluorescent light emanating from the first patch in the second well, from the second patches in the first well and the second well, and from a remainder of the biosensor; isolating fluorescent light emanating from the first patch in the second well from fluorescent light emanating from the first patch in the first well, from fluorescent light emanating from the second patches in the first well and the second well, and from fluorescent light emanating from a remainder of the biosensor; isolating fluorescent light emanating from the second patch in the first well from fluorescent light emanating from the second patch in the second well, from fluorescent light emanating from the first patches in the first well and the second well, and from fluorescent light emanating from a remainder of the biosensor; isolating fluorescent light emanating from the second patch in the second well from fluorescent light emanating from the second patch in the first well, from fluorescent light emanating from the first patches in the first well, and the second well, and from fluorescent light emanating from a remainder of the biosensor; detecting the fluorescent light emanating from the first patch in the first well with a first photodetector; detecting the fluorescent light emanating from the first patch in the second well with a second photodetector; detecting the fluorescent light emanating from the second patch in the first well with a third photodetector; detecting the fluorescent light emanating from the second patch in the second well with a fourth photodetector; analyzing the fluorescent light emanating from the first patch in the first well detected by the first photodetector in view of the fluorescent light emanating from the first patch in the second well detected by the second photodetector to determine a concentration of the first analyte in the sample; and analyzing the fluorescent light emanating from the second patch in the first well detected by the third photodetector in view of the fluorescent light emanating from the second patch in the second well detected by the fourth photodetector to determine a concentration of the second analyte in the sample.

In an alternative embodiment of the previous method for determining the concentration of several analytes in a sample, the biosensor defines a third well and a plurality of patches disposed within the third well, the third well containing a first patch of the plurality of patches having the first type of capture molecule associated therewith and a second patch of the plurality of patches having the second type capture molecule associate therewith. The method then further comprises the steps of: introducing a second liquid having second known quantities of the first analyte and the second analyte into the third well; introducing the at least one type of tracer molecule into the third well; isolating fluorescent light emanating from the first patch in the third well from fluorescent light emanating from the second patch in the third well, from fluorescent light emanating from the first patches in the first well and the second well, from light emanating from the second patch in the second well, and from fluorescent light emanating from the remainder of the biosensor; isolating fluorescent light emanating from the second patch in the third well from fluorescent light emanating from the first patch in the third well, from fluorescent light emanating from the first patches in the first well and the second well, from light emanating from the second patches in the first well and the second well and a remaining portion of the biosensor; detecting the fluorescent light emanating from the first patch in the third well with a fifth photodetector; detecting the fluorescent light emanating from the second patch in the third well with a sixth photodetector; analyzing the fluorescent light emanating from the first patch in the first well by the first photodetector in view of the light emanating from the first patch in the second well detected by the second photodetector and the fluorescent light emanating from the first patch in the third well detected by the fifth photodetector to determine a concentration of the first analyte in the sample; and analyzing the fluorescent light emanating from the second patch in the first well detected by the third photodetector in view of the fluorescent light emanating from the second patch in the second well detected by the fourth photodetector and the fluorescent light emanating from the second patch in the third well detected by the sixth photodetector to determine a concentration of the second analyte in the sample.

The invention further includes a method of detecting light emanating from a discrete area of a biosensor which subsequently passes through a waveguide. This method includes one or more of the following steps, either individually or in combination: isolating the light emanating from the discrete area of the biosensor from other light emanating from the remainder of the biosensor; directing the light emanating from the discrete area of the biosensor to a photodetector; and detecting the light emanating from the discrete area of the biosensor with the photodetector.

In a further embodiment of the method, the light emanating from the discrete area of the biosensor is isolated from other light emanating from the remainder of the biosensor by means of a structure which defines an inlet opening therein and a channel associated with the inlet opening, the inlet opening being positioned adjacent the discrete area of the biosensor, whereby light emanating from the discrete area passes through the inlet opening and thereafter through the channel to the photodetector. In yet another embodiment of this method, the light emanating from the discrete area of the biosensor is directed to the photodetector by at least one lens associated optically and interposed between the discrete area of the biosensor and the photodetector. In another embodiment, a filter is interposed between the discrete area of the biosensor and the photodetector.

The apparatus of the invention is directed to detecting fluorescence emanating from a discrete area of a biosensor, the apparatus comprising one or more of the following elements: a grate, optically associated with the discrete area of the biosensor, for segregating the fluorescent light emanating from the discrete area of the biosensor from light emanating from other areas of the biosensor, and structure for focussing the light, segregated by the grate, onto a photodetector. In some embodiments of the invention, the apparatus may also include structure selected from the group of a lens, mirror, fiber optic cable, and combinations thereof.

Furthermore, the invention includes a method for determining analyte concentration in a biosensor having a waveguide with capture molecules coated in a first well therein. This method comprises one or more of the following steps, either individually or in combination: introducing a sample believed to contain an analyte into the first well; introducing a tracer molecule, comprising a fluorescent label bonded to a molecule that binds with either the capture molecule or the analyte, into the first well; directing light through the waveguide, the light being of a wavelength which will excite the fluorescent label; detecting fluorescent light in the first well; and analyzing the fluorescent light to determine the analyte concentration.

This latter method may be modified whereby the waveguide includes capture molecules coated with a second well defined therein, the modified method further including the steps of: introducing a first liquid containing a first predetermined concentration of the analyte into the second well; introducing the tracer molecule comprising the fluorescent label bonded to a molecule that binds with either the capture molecule or the analyte into the second well; detecting fluorescent light in the second well; and analyzing the fluorescent light emanating from the first well in view of fluorescent light emanating from the second well in order to determine the analyte concentration in the first well.

This method may also be modified to include the step of segregating the fluorescent light emanating from the first well from fluorescent light emanating from the second well.

Furthermore, in other embodiments the method may include the step of directing the fluorescent light emanating from the first well to a first photodetector and directing the fluorescent light emanating from the second well to a second photodetector.

Yet another embodiment of the invention utilizes a waveguide in which capture molecules are coated in a third well defined therein. This particular embodiment further comprises: introducing a second liquid containing a second predetermined concentration of the analyte into the third well; introducing the tracer molecule comprising the fluorescent label bonded to a molecule that binds with either the capture molecule or the analyte into the third well; detecting fluorescent light in the third well; and analyzing the fluorescent light emanating from the third well in view of the fluorescent light emanating from the second well and the third well in order to determine the analyte concentration in the first well.

Each of the methods described above may be modified to include the step of simultaneously introducing the sample and the tracer molecule into the first well. In those embodiments which include a first liquid, the first liquid and the tracer molecule may be simultaneously introduced into the second well. In those embodiments which utilize a second liquid, the second liquid and the tracer molecule may be simultaneously introduced into the third well. Furthermore, in some embodiments, the steps of segregating the fluorescent light emanating from the first well, the fluorescent light emanating from the second well, and the fluorescent light emanating from the third well from one another as well as from fluorescent light emanating from a remainder of the biosensor may form part of the inventive method. This method may be further modified to include the step of directing the fluorescent light emanating from the first well to a first photodetector, directing the fluorescent light emanating from the second well to a second photodetector, and directing the fluorescent light emanating from the third well to a third photodetector.

The system includes an optical detection system that detects fluorescence from fluorescent binding assays in a biosensor. A processing system and method may be used to determine analyte concentration from the fluorescence detected by the optical detection system. The system and method may involve detecting fluorescence from multiple channels or wells. In one embodiment, the system and method involves detecting fluorescence in three channels or wells, including a variable value, a maximum value, and a minimum value. The optical detection system may include photodetectors with or without in series lenses. Alternatively, a CCD camera may be used.

BRIEF DESCRIPTION OF DRAWINGS

FIG. 5 is a side-view in cross-section of a biosensor in combination with an optical detection system.

FIG. 6 is a top view of a channeling device and photodetector employed in the system of FIG. 5.

FIG. 7 is an end view in cross-section of the system of FIG. 3, taken along section line 7—7.

BEST MODES FOR CARRYING OUT THE INVENTION

Figure 1:
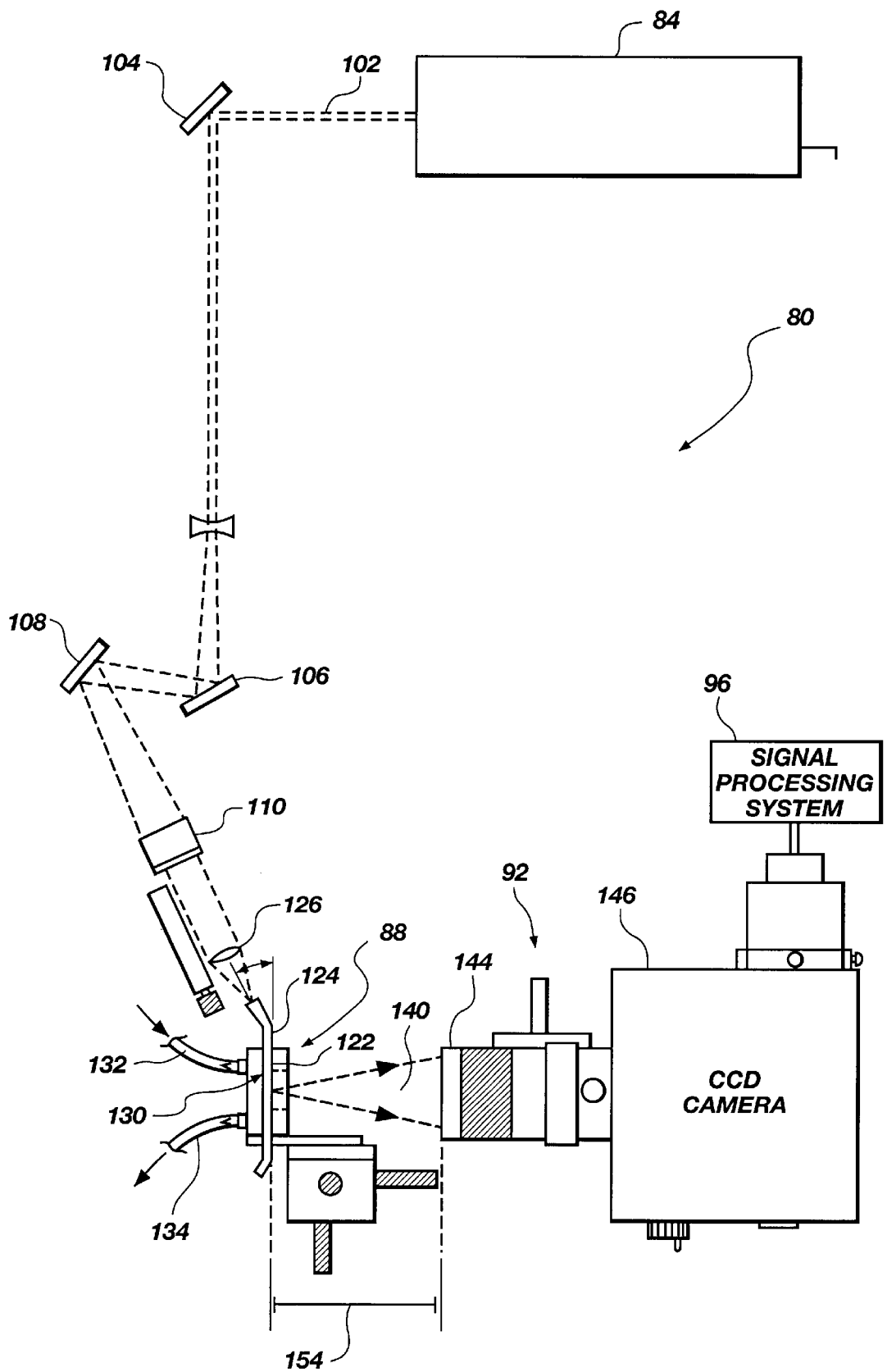
FIG. 1 is a schematic diagram of a fluorescent immunoassay apparatus according to one embodiment of the invention.

Referring to FIG. 1, a biosensing system, generally 80, includes a light source 84, a biosensor 88, and an optical detection system 92. As used herein, the term "light" refers to electromagnetic radiation, and is not limited to the visible spectrum. Biosensor 88 contains an assay that emits fluorescence when excited by light from light source 84 depending on whether or not analyte is present in a liquid sample being analyzed in the biosensor. The fluorescence is detected by an optical detection system 92. Biosensing system 80 may further include a signal processing system 96 that analyzes signals from optical detection system 92.

A. Overview of System Components

In one embodiment, light source 84 is a laser that produces a light beam 102 that is directed by means of mirrors 104, 106, and 108 to biosensor 88. A 45° angle mirror 110 may be positioned for making beam 102 a vertical beam prior to focussing the beam onto biosensor 88.

Biosensor 88 includes an optical substrate or waveguide 122 with one end 124 thereof positioned to receive light beam 102. A focussing lens 126 is positioned between angle mirror 110 and end 124 of waveguide 122, for focussing light beam from 102 onto end 124. Focussing lens 126 is here shown mounted on an X-Y translation unit so that its position may be adjusted for best focussing, although an X-Y translation unit is not required.

Figure 2:
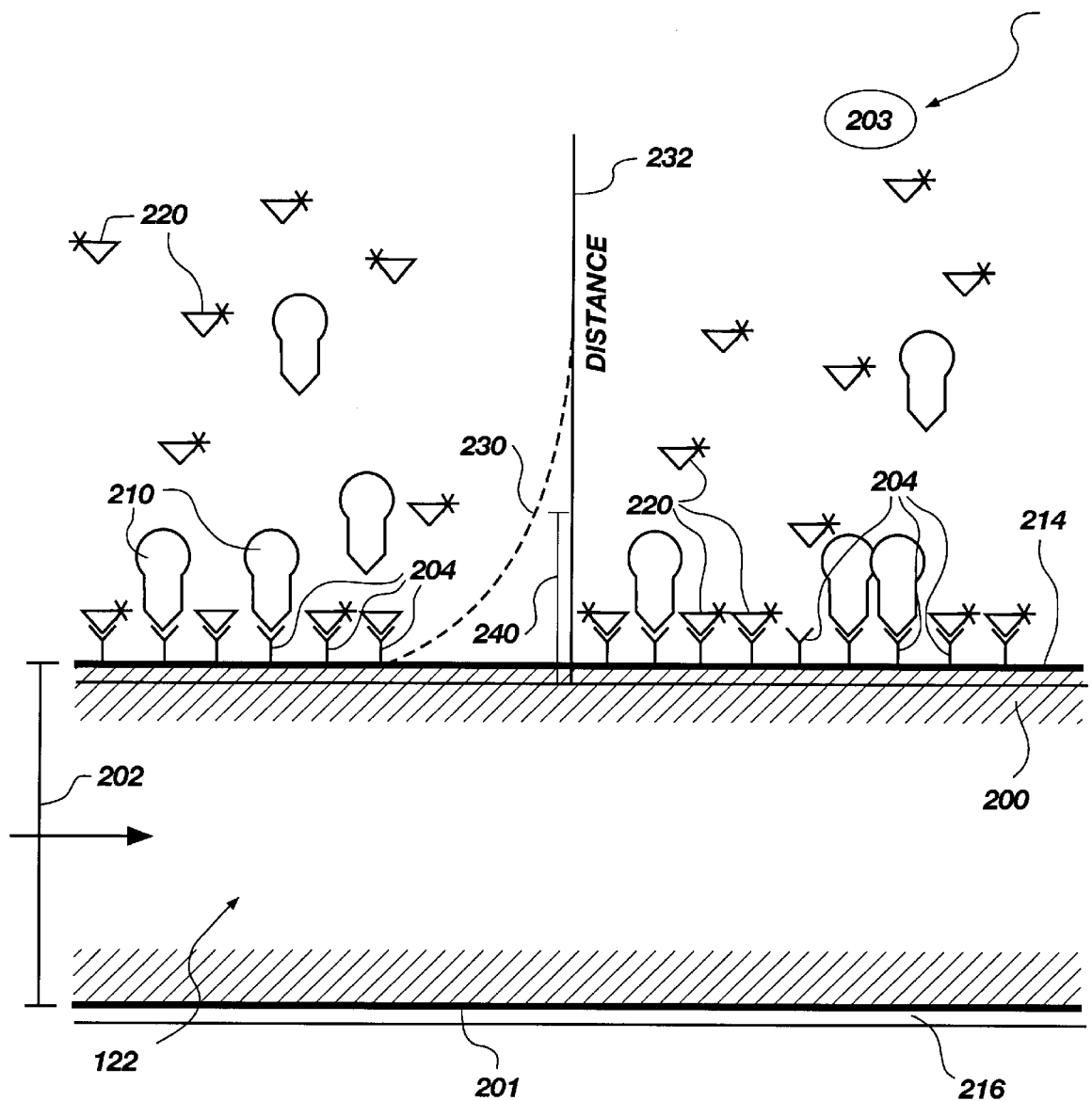
FIG. 2 is an enlarged, stylized side view of a portion of a biosensor and biochemical components that may be used in some embodiments of the invention.

In a preferred embodiment, waveguide 122 has a generally planar portion having two planar surfaces 200, 201 spaced by a width 202, as shown in FIG. 2. However, waveguide 122 could be a solid or rod-shaped fiber optic. Waveguide 122 may, for example, be a square or rectangular glass microscope slide or coverslip, or the like. Materials for waveguide 122 include glass, high-lead glass, quartz, optical plastic, and the like as are well-known in the art.

It will be understood by those skilled in the art that the number and arrangement of mirrors 104, 106, 108, and 110, and lens 126 and other components may be varied as necessary or desirable to accommodate various space or other limitations, with the sole requirement being that a sufficient amount of light be directed to biosensor 88. Further, the sizes of the various components of FIG. 1 are not to scale.

Figure 3:
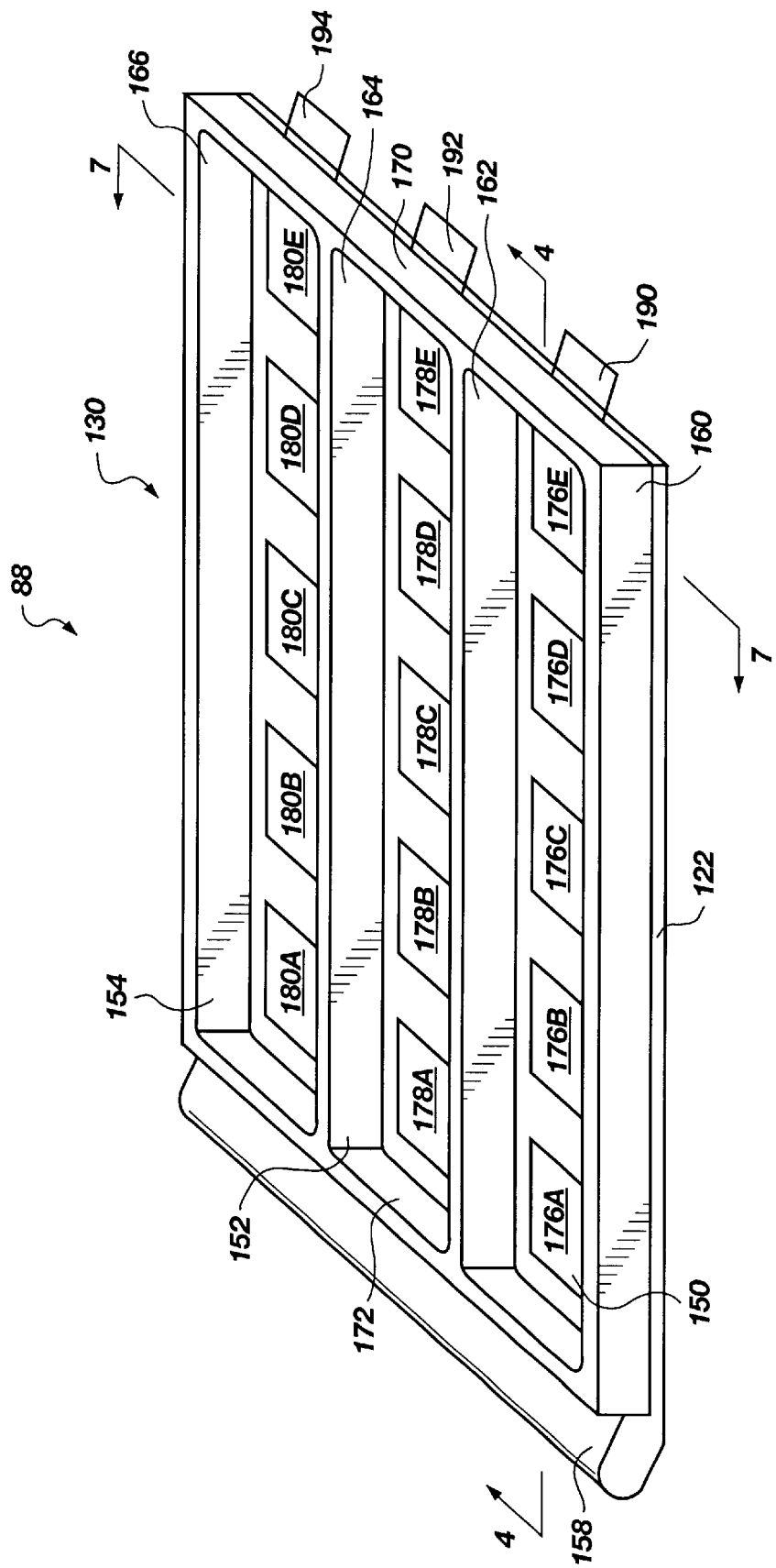
FIG. 3 is a perspective view of a biosensor that may be used in some embodiments of the invention.

In a preferred embodiment, biosensor 88 includes a tray-shaped waveguide 130 in which the assay is held that produces fluorescent radiation when exited (FIG. 3). The fluid to be analyzed with the assay (e.g. biological liquids such as whole blood or blood components such as plasma), may enter tray 130 through an inlet tube 132 and exit tray 130 through an outlet tube 134 (FIG. 1) in fluid communication with the tray.

Optical detection system 92 is positioned to detect fluorescent light 140 emitted from the assay in tray 130. As shown in FIG. 1, optical detection system 92 includes a collection lens 144. As shown, detector 146 may be a CCD (charge-coupled device) camera detector 146. Collection lens 144 is positioned to collect the emitted fluorescence from a direction substantially orthogonal to the direction of propagation of light beam 102 through optical substrate 122.

The distance 154 between collection lens 144 and optical substrate or waveguide 122 is selected as known to those skilled in the art to maximize the collection of light emitted from the region of evanescent light penetration while at the same time imaging this light onto the photodetection face. The light collected by collection lens 144 is transmitted to detector 146, which responds by outputting signals reflective of the level of collected fluorescent light. Such signal collection provides simultaneous measurement of multiple samples in a much simpler way than a system in which a separate optical element is needed to read each well or patch.

The present optical detection system also provides for collection of emitted fluorescence directly from the evanescent zone 240 (FIG. 2), rather than via evanescent penetration of the fluorescence into the waveguide.

As opposed to including collection lens 144 and detector 146, optical detection system 92 may include any type of photodetector useful to detect light in the wavelength region spanning the wavelength range of the emitted fluorescence. Optical detection system 92 may include an imaging-type detector providing direct imaging of each of the fluorescent signal(s) originating in the evanescent zone. Alternatively, a non-imaging detector may be used as described herein.

Alternatively, optical detection system 92 may be a photomultiplier, a semiconductor photodiode, or an array of such detectors. In embodiments other than a CCD, an array is generally preferable to a single detector for some purposes. With an array of small detectors, the user can determine that the maximum fluorescence is being detected and is not inadvertently missed due to misalignment of the collection and detection optics. Optionally, a grating spectrograph is coupled to the CCD or other detection means, to provide spectral analysis of the detected light. In that case, means are also provided to integrate the signal function around each peak to determine the total collected fluorescence from a sample. Alternatively, in an embodiment for use in a setting such as in a testing laboratory, and for which all of the parameters of the assay have been standardized, the spectrograph may be replaced by a filter (or filters) which passes only wavelengths in the region of tracer fluorescence.

Details of various optical detection systems will be described after providing an overview of fluorescence.

B. Overview of Fluorescence

Referring to FIG. 2, the waveguide portion 122 is embodied as a waveguide having at least one planar surface 200 spaced from a second surface 201 by a width 202. Waveguide 122 is preferably solid, but may include a hollow section through which the light travels if such hollow section is filled with a substance whose index of refraction is equal to or higher than that of the waveguide. At least surface 200 is disposed in contact with a sample solution 203. A plurality of capture molecules 204 are immobilized on surface 200. The sample solution contains a plurality of analyte molecules 210 of a selected analyte and a plurality of tracer molecules 220. The capture molecules are chosen or constructed to bind to a binding moiety present on each of the analyte molecules 210. Depending on the type of assay being conducted, a portion of the tracer molecules either react with the capture molecules or the analyte molecules. The tracer molecule 220 is chosen or constructed to emit fluorescent light in response to stimulation by light of the appropriate wavelength. The level of fluorescence emitted by the tracer molecules 220 is a measure of the amount of analyte bound to the capture molecule and is thereby reflective of the concentration of analyte molecules 210 in the solution.

Light source 84 may be an argon laser capable of emitting light at wavelengths of between about 488 nm and 514.5 nm (nanometers). In an alternate embodiment, light source 84 is a laser diode or similar device emitting at center wavelengths of 600 nm to about 900 nm. Depending on the requirements of the fluorescent tracer, light source 84 may also be embodied as any other laser or other high-intensity light source emitting a sufficient amount of light at an appropriate wavelength to excite the selected tracer.

When light is propagated in waveguide 122 and totally internally reflected at surfaces 200 and 201, an evanescent light field is produced having an intensity curve 230 that drops off with distance from surface 200, as diagramed relative to a distance axis 232. An evanescent zone 240 is the only region of the solution in which the evanescent light intensity is sufficient to excite a significant or detectable fraction of tracer molecules 220 (not to scale). Tracer molecules 220 outside evanscent zone 240 will contribute little or no induced fluorescence. Evanscent zone 240 is typically between about 1000 Å and 2000 Å in depth.

Capture molecules 204 are reactive with the analyte molecules 210, and may be whole antibodies, antibody fragments such as Fab' fragments, peptides, epitopes, membrane receptors, whole antigenic molecules (haptens) or antigenic fragments, oligopeptides, oligonucleotides, mimitopes, nucleic acids and/or mixtures thereof. Capture molecules 204 may also be a receptor molecule of the kind usually found on a cell or organelle membrane and which has specificity for a desired analyte, or a portion thereof carrying the analyte-specific-binding property of the receptor.

In FIG. 2, a competition assay scheme is depicted (also termed a displacement assay). However, as will be apparent to the skilled person, alternate assay schemes such as sandwich assays may be performed with the present apparatus. See, e.g. U.S. Pat. Nos. 4,376,110 and 4,486,530 to Hybritech, Inc. for a description of sandwich assays.

The capture molecules 204 may be immobilized on the surface 200 by any method known in the art. However, in the preferred embodiment the capture molecules are immobilized in a site-specific manner. As used in this application, the term "site-specific" means that specific sites on the capture molecules are involved in the coupling to the waveguide, rather than random sites as with typical prior art methods.

Tray 130 may include a thin surface layer 214 that interfaces with surface 200 of waveguide 122. Surface 214 has an index of refraction which is equal to or higher than that of waveguide 122, and is useful in improving the optical or chemical properties of surface 200. Likewise, a surface 216 may be applied below surface 201 to prevent scratching thereof. Surface 216 may have an index of refraction which is higher, lower, or equal to that of waveguide 122.

C. Details of Biosensor

FIG. 3 illustrates a particular embodiment of biosensor 88 that includes tray 130 and associated waveguide 122. A lens 158 receives light from the excitation source, as more fully described in connection with FIG. 4. The depicted tray 130 includes three wells: well 150, well 152, and well 154.

Walls 160, 162, 164, and 166 define side boundaries for wells 150, 152, and 154. Walls 170 and 172 define frame and rear boundaries for wells 150, 152, and 154. In one embodiment of the invention, described herein, fluorescence measurements from three wells are used to determine analyte concentration. In that embodiment, one well is a blank well (e.g. well 150), one well is a measurement well (e.g. well 152), and one well is a high calibration well (e.g. well 154). In another embodiment, fluorescence measurements from two wells (e.g. a blank well and a measurement well) are used to determine analyte concentration. In yet another embodiment fluorescence measurements from only one well, i.e. the measurement well, may be used to determine analyte presence and/or concentration. There may be more than three wells in a tray (e.g. from two to ten), but depending on the embodiment or embodiments used, particular groups of two or three wells in a tray may be treated as a set.

Each of wells 150, 152, and 154 is shown as comprising or defining five zones therein. Each zone contains a respective patch. Well 150 includes patches 176A, 176B, 176C, 176D, and 176E. Well 152 includes patches 178A, 178B, 178C, 178D, and 178E. Well 154 includes patches 180A, 180B, 180C, 180D, and 180E. Each patch contains a different capture molecule species (Fabs or Fab' fragments) on which fluorescence may occur. Although FIG. 3 illustrates wells wherein each well defines five zones, it should be understood that biosensor 88 may include wells having greater or fewer than five zones (e.g. only one zone). Different zones may be used to test for different analytes.

Also, two or more zones may be used to test for the concentration of the same analyte.

Figure 4:
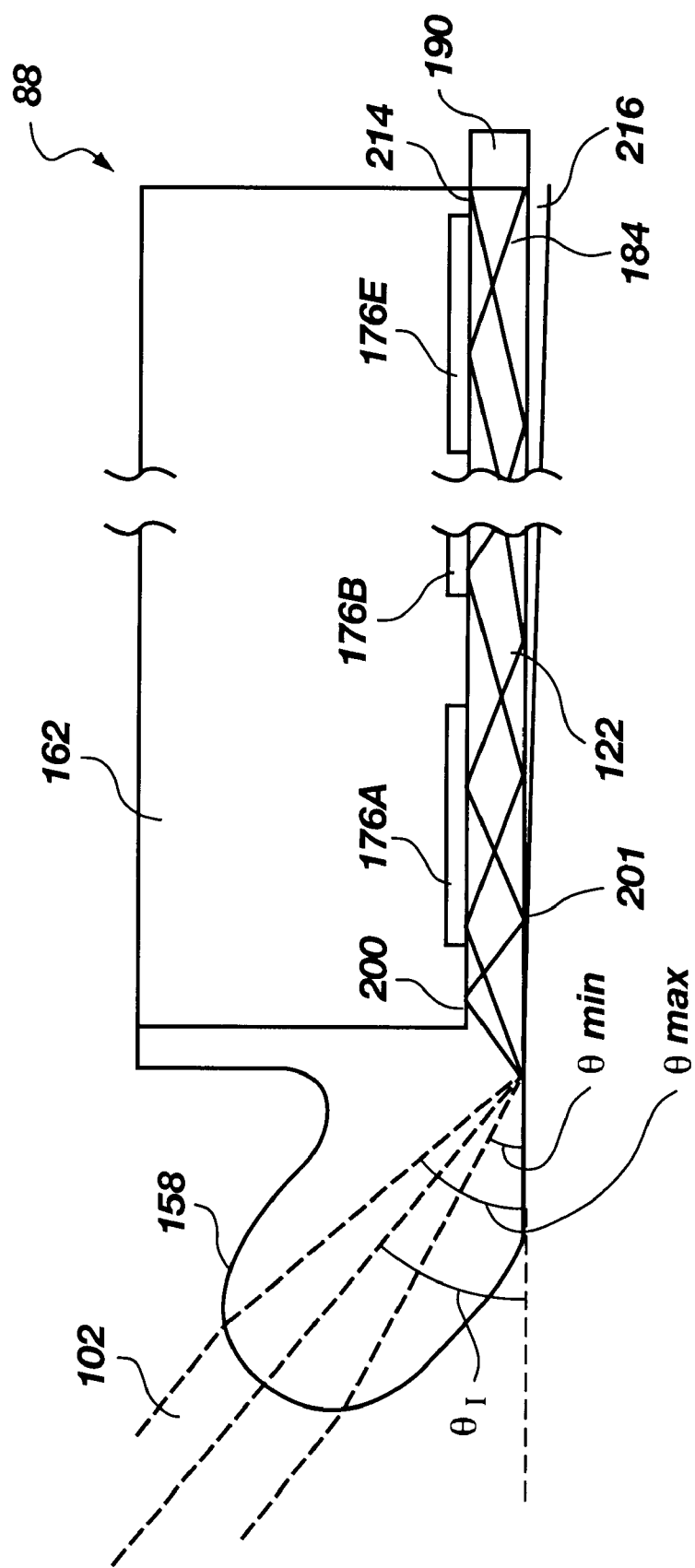
FIG. 4 is a sectional view of a portion of the biosensor of FIG. 3 shown in more detail, taken along section line 3—3.

FIG. 4 is a side view of biosensor 88 taken along line 4—4 of FIG. 3 (although the dimensions are not to scale for ease in illustration). Referring to FIG. 4, the purpose of lens 158 is to receive light beam 102 and create a beam 184 that travels in waveguide 122 with total internal reflection. As described in connection with FIG. 2, beam 184 creates an evanescent light field that extends into solution 203. Generally, the most accurate results are obtained if beam 184 reflects uniformly throughout surface 200, rather than merely on isolated spots on surface 200. This is the case, because measurements are based on an average of a large number of hits which reduces the possibility of inaccurate results from aberrations.

To accomplish these objectives, the axis of lens 158 is positioned at an incident angle $\theta_I$ with respect to waveguide 122. The refractive effect of the lens is such that beam 102 is channelled to a beam 184, which is composed of a cone of rays at different angles from $\theta_{MIN}$ through $\theta_{MAX}$. The angle $\theta_I$ is chosen such that $\theta_{MAX}$ is less than critical angle $\theta_C$ for total internal reflection. The effect of the spread in ray angles is to broaden the beam as it travels by TIR down the waveguide, thus making the bounce less discrete and the surface illumination more uniform. On the one hand, if the difference between $\theta_{MIN}$ and $\theta_{MAX}$ is too small, beam 184 will not broaden enough to uniformly hit surface 200. On the other hand, if the difference between $\theta_{MIN}$ and $\theta_{MAX}$ is too great, the evanescent light field is reduced because much of the rays of beam 184 will be have an angle far less than $\theta_C$ and will reflect a relatively small number of times through waveguide 122.

The values for the various angles depends on the indices of refraction of the materials involved. Merely as an example, the index of refraction of waveguide 122 may be about 1.59 to 1.60, and the index of refraction of the material surrounding waveguide 122 may be about 1.33. This leads to a $\theta_C$ of about 32°. Under such an example, an incident angle $\theta_I$ of about 23° to 25° may lead to satisfactory results.

The critical angle is controlled by the relative indices of refraction of waveguide 122 and those materials interfacing with waveguide 122. Where the material above surface 200 has a different index of refraction than the material below surface 201, there will be two critical angles, and $\theta_{MAX}$ should be less than both critical angles. Tray 130 may include a thin surface layer 214 (having an index of refraction which is equal to or higher than that of waveguide 122) that interfaces with surface 200 of waveguide 122 to improve the optical or chemical quality of surface 200. Alternatively, patches 176A, etc. and solution 203 may directly contact surface 200. In that case, solution 203 and patches 176A etc. would need a lower index of refraction than that of waveguide 122. Likewise, if used, surface 216 below surface 201 may be used to prevent scratches to surface 201, and would have an index of refraction higher, lower, or equal to that of waveguide 122. Otherwise, air would provide an adequate interface.

Optical detection devices such as lenses and photodiodes 190, 192, and 194 may be used at the end of waveguide 122 to detect whether a sufficient amount of light is passing through waveguide 122. Alternately, channeling devices may be used to collect light for each photodiode. Alternatively, as is described herein, a detector in the fifth zone of a channel may be used to detect the quantity of light passing through the waveguide.

Reflectors may be used in place of photodiodes 190, 192, and 194 to reflect some or all of beam 184 back into waveguide 122.

Biosensor 88 is only one example of a suitable biosensor. For example, lens 158 is only one means of providing a proper beam 184 to optical waveguide 122. Rather than have lens 158 at an angle, mirrors could create the angle.

D. Optical Detection Systems Employing Photodetectors

Referring to FIG. 5, biosensor 88 is positioned above an optical detection system 241. Optical detection system 241 is shown in cross-section in FIG. 5. Optical detection devices such as photodetectors 244A, 244B, 244C, 244D, and 244E receive fluorescent light from well 150. Spacer support plates 246 and 248 space biosensor 88 from an optical narrowband filter, which passes only those frequencies around a certain range corresponding to the fluorescence from well 150. The filter 250 blocks other frequencies including those of beam 102, which may pass from waveguide 122 because of, for example, imperfections in surface 201. Filter 250 may be constructed of numerous thin film dielectric layers.

A tunnel 254A is created below ZONE 1 by support 246, a side baffle (or baffle section) 260, a back baffle (or baffle section) 262, and a front baffle (or baffle section) (not shown). The baffles are fabricated from opaque material to prevent crossover of light between neighboring tunnels. A cross-section of tunnel 254A parallel to waveguide 122 may be rectangular, circular, or some other shape.

A channeled tunnel 258A is created beneath tunnel 254A by a channeling device 264A, a top view of which is shown along lines 6—6 in FIG. 6.

Exemplary rays of light from ZONE 3 are shown in tunnel 254C and channelled tunnel 258C.

Referring to FIG. 6, a cross-section of channeling device 264A is circular and narrows toward photodiode 244A. Ideally, the shape of channeling device 264A is designed to maximize the amount of light channeled to photodiode 244A. However, spherical, elliptical, and parabolic reflectors, while not optimum, are cheaper and adequate. As such, channeling device 264A would be a non-imaging reflector. However, channeling device 264A under a different construction could be an imaging reflector, although perhaps at greater expense and with a lower amount of light channeled for photodetector 244A. Channeling device 264A may be formed of more than one piece. Channeling device 264A may be made of plastic with an aluminum coating, which may be applied through film evaporation.

Tunnels 254B, 254C, 254D, and 254E are created beneath zones 2, 3, 4, and 5 and are analogous to tunnel 254A. Likewise, channelled tunnels 258B, 258C, 258D, and 258E are created by channeling devices beneath filter 250 and tunnels 254B, 254C, 254D, and 254E, and are analogous to channelled tunnel 258A.

An imaginary line 256 that is normal to waveguide 122 is provided as a reference. As previously noted, a filter 250 blocks frequencies other than those in a narrow band. However, the filter 250 passes frequencies that should be blocked if the light having those frequencies has an angle greater than a maximum with respect to the normal line 256. A purpose of tunnel 254A is to eliminate light having an angle greater than the maximum. This is accomplished by spacing filter 250 at a sufficient distance from waveguide 122 and by providing the inside of tunnel 254A with a light absorbing, rather than a light reflecting, material.

To avoid broadening the passband of filter 250, a f# value of the collection should be kept above a minimum value. The value f# is approximately equal to L/D, where L is the distance between waveguide 122 and filter 250, and D is the width of the particular tunnel 254A through tunnel 254E that is above the photodetector of interest. A large f# is desirable because filter 250 will pass little unwanted light. However, a large f# leads to there being a small amount of light collected. Accordingly, L and D are chosen to provide an f# value that is large enough, but not too large.

In this regard, channeling devices 258A through 258E are optional. They increase the collection efficiency of the photodetectors (since the photodetectors will accept light within a broad cone of angles), if the area of the photodetectors is smaller than the cross-sectional area of the tunnels. Depending on the test made, it would be possible to include channeling devices for some photodiodes but not others. Moreover, the distances D and/or L do not have to be identical for each zone. Further, different filters could be used for different zones. Another option is to use a wider photodetector as opposed to a channeling device.

There is another array of five photodetectors beneath zones 1 through 5 of well 152, and a third array of five photodetectors beneath zones 1 through 5 of well 154.

Although only one photodetector is shown beneath each zone, there could be more than one. For example, two or more photodetectors could replace photodetector 244A at the bottom of channeling device 264A.

One of the zones, for example zone 5, may be dedicated to detecting the amount of light in waveguide 122 without the presence of any bound antibody. Bumps, micromirrors, or a diffraction grating could be fabricated in zone 5 to deflect all or a known portion of the light in waveguide 122 into the photodetector 244E beneath this zone. This could be an alternative to the use of detectors 190–194.

FIG. 7 is an end view of biosensor 88, taken along line 7—7 of FIG. 3 and extending into an associated optical detection system. Additional photodetectors may be associated with additional channeling devices.

Figure 8:
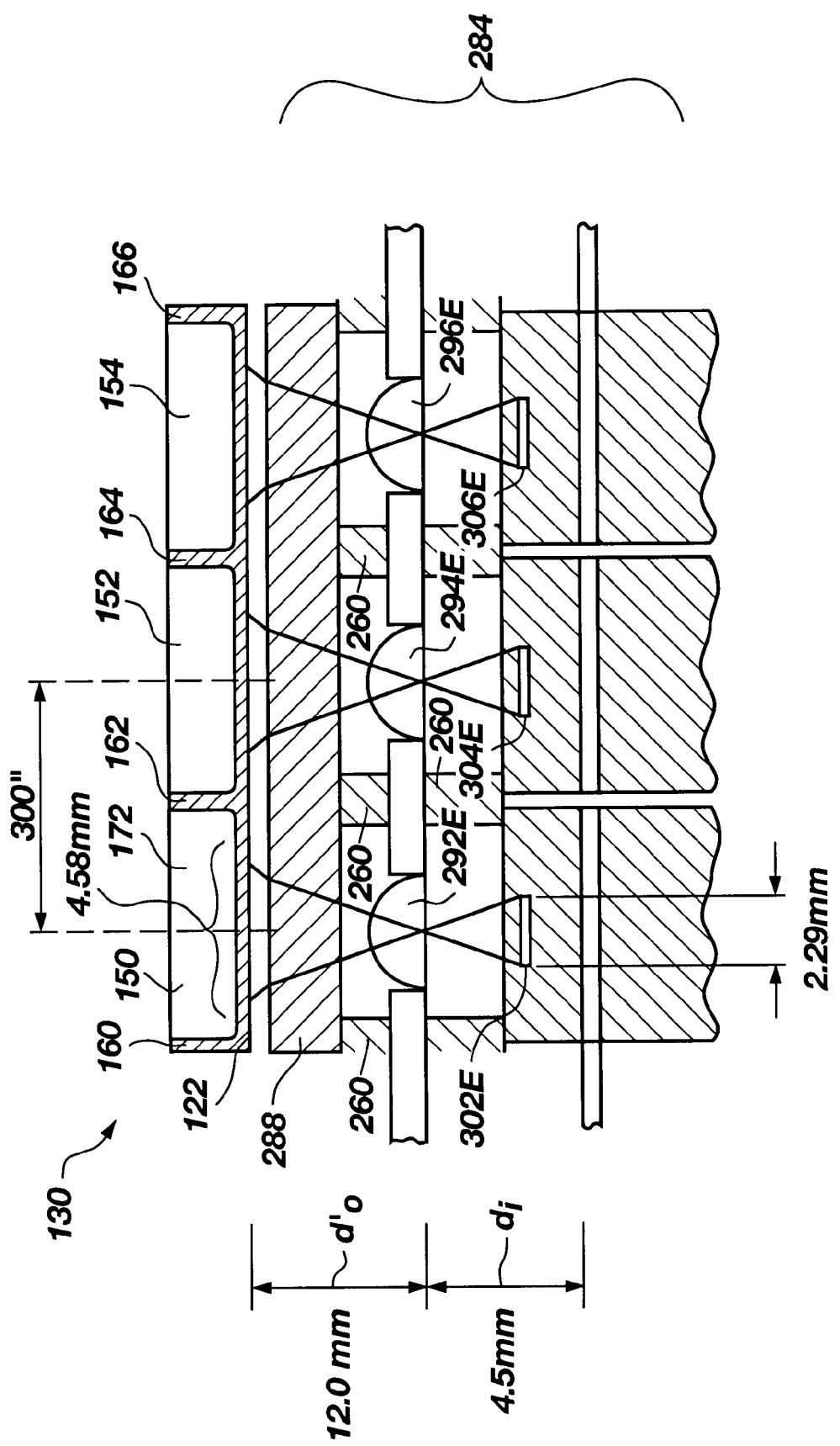
FIG. 8 is an end view of a biosensor with an alternative optical detection system.

FIG. 8 illustrates an end view of biosensor 88 in combination with an optical detection system 284, which is an alternative to optical detection system 241. Referring to FIG. 8, a narrow band filter 288 is positioned intermediate the wave guide 122 and the lenses 292E through 296E. As shown the filter 288 may be positioned next to waveguide 122. Filter 288 passes desired fluorescent frequencies and blocks other frequencies. Fluorescent light from channels 150, 152, and 154 passes through waveguide 122 and lenses 292E, 294E, and 296E to photodiodes 302E, 304E, and 306E. Baffles 260 may be used to preclude light emanating from other wells from mixing with the light emanating from a given well. Lenses 292E, 294E, and 296E are preferably high collection efficient high numerical aperture lenses, but other suitable lenses may be used. Photodiodes 302E, 304E, and 306E are shown embedded in OPT209 IC assemblies marketed by Burr Brown.

Suitable lengths and distances of the components of optical detection system 284 may be selected as follows. Under the lens law $1/d_i+1/d_o=1/f$ where $d_i$ is the distance from the lens to the image plane, $d_o$ is the distance from the lens to the object, and f is the focal length of the lens. In the case of a magnification of ½, $d_o= 2d_i$. Therefore, $f=2d_i/3$. Where f=3 mm, then $d_i$=4.5 mm, and $d_o$=9 mm. However, to account for the index of refraction n of filter 288 (6 mm thick, n=1.5), add (1.5−1.0)×6=3 mm, so that $d_o$=9 mm+3 mm=12 mm.

E. Signal Processing System

1. Exemplary Hardware

Figure 9:
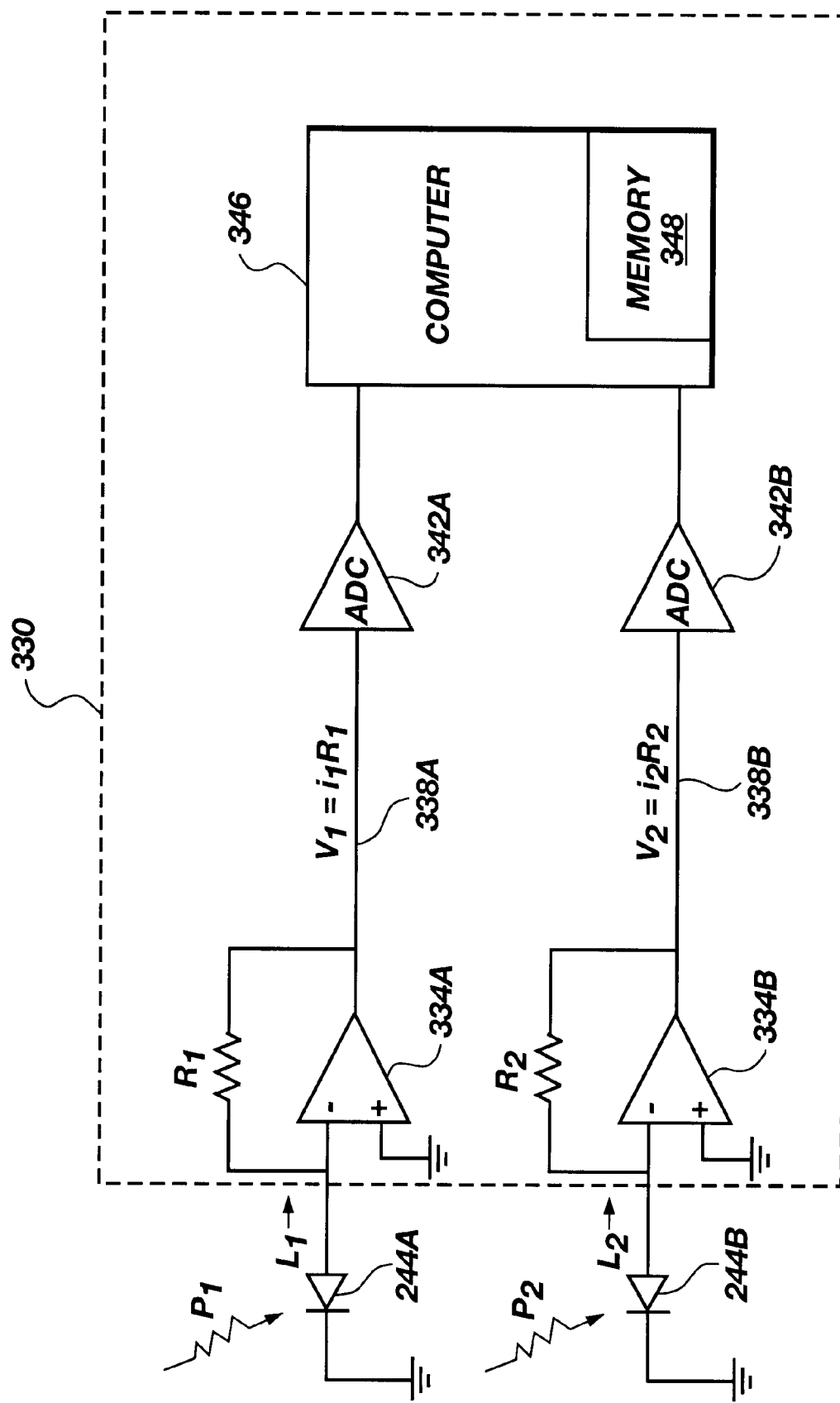
FIG. 9 is an electrical schematic of a processing system that may be employed in some embodiments of the invention.

Referring to FIG. 9, a signal processing system 330 is analogous to signal processing system 96 in FIG. 1. Photodetectors 244A and 244B are representative of the various photodetectors in FIG. 5. Although only two photodetectors are shown for ease of illustration, signal processing system 330 would have several photodetectors, in almost every instance. Photodetector 244A detects light having optical power $P_1$ and photodetector 244B detects light having optical power $P_2$. Photodetectors 244A and 244B produce currents $i_1$ and $i_2$, respectively, which are a function of optical powers $P_1$ and $P_2$.

Transimpedance operational amplifiers (op amps) 334A and 334B or similar devices provide voltages $v_1$ and $v_2$ to conductors 338A and 338B, respectively, where $v_1=i_1R_1$ and $v_2=i_2R_2$. The resistance values of $R_1$ and $R_2$ may be identical or different, depending on the test being conducted. A 1 MΩ value may be suitable for many purposes. An example of photodetector 244A and op amp 334A are contained on a photodetector chip marketed by Burr Brown as a OPT209 device. Such a chip includes a resistance value of 1 MΩ and includes connections to provide an external resistor. Alternatively, for example, an array of dies for numerous photodetectors may be wire bonded to a substrate, or an array of photodetectors could be formed of a single piece of silicon.

Analog-to-digital convertors (ADCs) 342A and 342B convert voltages $v_1$ and $v_2$ to digital values for processing to a computer 346 having a memory 348.

Of course, the details described in connection with processing system 330 are merely examples. Various other components and techniques may be used. For example, an analog phase sensitive detector (also called a lock-in amplifier and synchronous detector) or other device in which an output is a function of current could be employed in place of op amps. The analog phase sensitive detector may be used in connection with a pulsed on/off light source or a mechanically chopped light source. The analog phase sensitive detector has the advantage of averaging before conversion to digital format. Accordingly, it may produce a more accurate result and a slower ADC with fewer bits may be used.

Photodetectors 244A–244E could be "on" (sensitive to light) simultaneously or sequentially (one at a time). Still alternatively, they could be "on" in groups.

2. Computations

The analyte concentration [A] of the analyte of interest and may be determined as follows.

a. Determination of the Affinity Constant $K_A$

The affinity constant $K_A$ is a measure of how well antibodies couple to analytes. Under a preferred procedure, a value of $K_A$ is determined at the manufacturing level of tray 130 and applying the patches. (Note that tray 130 and waveguide 122 may be sold together or separately, but in the following discussion it is assumed that a particular waveguide is joined with a particular tray and once a tray is used, the waveguide will be disposed of with the tray.) The value of $K_A$ and an error associated therewith is supplied to an end user (such as in a clinic or hospital) in, for example, a bar code that accompanies tray 130.

The value of a $K_A$ may be determined at the manufacturing level as follows. The fraction of bound antibody active sites ($f_b$) in a solution in tray 130 may be expressed in equation (1):

$$f_b=K_A[A]/(1+K_A[A]) \qquad (1),$$

where $K_A$ is the affinity constant, and [A] is the analyte concentration.

Solutions of, for example, progressively larger known analyte concentrations $[A]_1, [A]_2, \ldots, [A]_N$ are passed through an antibody well 152 (one solution per well) of a particular tray 130 (in combination with an associated waveguide), referred to as tray 130-1. Photodetection means determine corresponding fluorescence intensities $I_{VAR1}$, $I_{VAR2}, \ldots, I_{VARN}$ associated with each of the varying concentration solutions. (Either only one photodetector per well or more than one photodetector per well can make measurements of intensity I.)

Photodetectors (such as are shown in FIGS. 4–8) or CCD 146 determine corresponding fluorescence intensities $I_{VAR2}$, $I_{VAR2}, \ldots, I_{VARN}$ associated with the solutions. (Either only one photodetector per well or more than one photodetector per well can make measurements of intensity I.) A solution with a known minimum analyte concentration is passed through well 150 and a solution with a known maximum analyte concentration is passed through well 152.

The process is repeated with progressively larger known analyte concentrations $[A]_1, [A]_2, \ldots, [A]_N$ passed through antibody well 152 of a tray 130-2, the photodetection means determines corresponding fluorescence intensities $I_{VAR1}$, $I_{VAR2}, \ldots, I_{VARN}$. Since a single test in each antibody well trays 130 are usually self-destructive to the antibody well 152 (or at least not cost effective to warrant stripping the bound analyte molecules from the capture molecules), it is preferable to use a plurality of trays 130 to generate the relationship (i.e., curve) between fraction of bound antibody active sites $f_b$ and concentration [A]. Using a plurality of trays 130 is also preferable from a quality control standpoint. Random selection of trays from a production run (wherein the same material lots are used to produce the trays) will render a statistically more accurate $f_b$ to [A] relationship (i.e., curve). Preferably, values for $I_{MIN}$ (zero or near zero concentration of the analyte of interest) and $I_{MAX}$ (maximum or saturated concentration of analyte of interest) are included in the known concentration solutions.

Thus, the values of $f_{b1}, f_{b2}, \ldots, f_{bN}$ are calculated according to equation (1) for each analyte concentration $[A]_1, [A]_2, \ldots, [A]_N$ for each of trays 130-1 through 130-X. The values of $f_{b1}$ for the various trays 130-1 through 130-X are averaged to create a $f_{b1-ave}$. Likewise, the values of $f_{b2}$ for the various trays 130-1 through 130-X are averaged to create a $f_{b2-ave}$, and so forth through the values of $f_{bN}$ being averaged to create a $f_{bN-ave}$.

The number "X" in tray 130-X may be a preset value based on experience and quality control considerations. Alternatively, the value of "X" may be increased if the standard deviation of various $f_b$ values is greater than a threshold. In that case, values of $f_b$ for additional trays would be determined and considered in a revised average.

In this respect, a relatively small number of trays from a batch of trays (or a group of batches of trays) are used to develop values $f_{b1-ave}, f_{b2-ave}$, and $f_{bN-ave}$ for the whole batch. The number of trays used in the determination of $f_{b1-ave}, f_{b2-ave}$, and $f_{bN-ave}$ vis-a-vis the total number of trays in a batch (or group of batches) will depend on various factors including the error that will be tolerated. That error will vary depending on the analyte of interest and other considerations. Well developed issues of quality control may also be considered.

Next, a value of $K_A$ should be determined from $f_{b1-ave}$, $f_{b2-ave}$, and $f_{bN-ave}$. Under equation (1), if $f_b$=0.5, then $K_A$=1/[A]. As an example, the affinity constant can be determined from matching $f_b$ and [A] through a non-linear curve fitting technique (such as the "least squares" method) on equation (1). $K_A$ may be used as a fitting parameter. $K_A$ is varied in the non-linear least squares process to determine a best fit. A standard error is also determined.

Alternatively, a best fit may be determined in a non-linear least squares for $I_{MIN}, I_{MAX}$, and $K_A$.

The value of $K_A$ and error may be encoded onto a bar code or other means, e.g., magnetic strip, or another optical indicator with digital readout that is supplied with each tray.

b. Determination of the Analyte Concentration in the Field

Biosensing system 80 with a signal processing system 96 may determine the analyte concentration as follows.

The invention also includes methods of manufacturing and using the device. The assay device housing preferably includes a bar code reader or like device. The reader is used to input factory calibration or like information into the assay device for each tray. Thus, it is preferable to have the factory calibration attached to or on each tray. The calibration information is used to calculate the concentration of the analyte of interest using the fluoroluminescent intensity of the low control sample, the high control sample, and one of the test samples.

Referring to FIG. 3, a solution having a minimum or zero analyte concentration is passed through the low control antibody well 150, a solution having a maximum analyte concentration is passed through the high control antibody well 154, and a solution having the analyte of interest is passed through the sample antibody well 152. The analyte concentration of the analyte of interest is unknown. The purpose of this aspect of the invention is to determine the analyte concentration of this analyte of interest. (Of course, the particular well chosen for minimum, maximum, and unknown does not matter.)

The value of $f_b$ is determined according to equation (2), below:

$$f_b = (I_{VAR} - I_{MIN})/(I_{MAX} - I_{MIN}) \qquad (2),$$

here $I_{VAR}$ is an intensity of fluorescent light radiated in response to evanescent light interacting with a solution having an unknown analyte concentration that is between a minimum and a maximum analyte concentration, inclusive; $I_{MIN}$ is the intensity of fluorescent light radiated in response to evanescent light encountering a solution having a minimum analyte concentration; $I_{MAX}$ is the intensity of fluorescent light radiated in response to evanescent light encountering a solution having a maximum analyte concentration.

Photodetectors or CCD 146 measure the intensity of the fluorescent light to produce $I_{MIN}$ and $I_{MAX}$ for the particular solutions in wells 150 and 154. Photodetectors or CCD 146 measure the intensity of the fluorescent light to produce $I_{VAR}$ for the sample solution in well 152.

The value of [A] may be solved for in equation (1), yielding equation (3):

$$[A] = f_b/((1-f_b)K_A) \qquad (3).$$

The value of $f_b$ is calculated by computer 346 according to equation (1) based on the measured values of $I_{MIN}, I_{VAR}$, and $I_{MAX}$ from wells 150, 152, and 154. The value of $K_A$ is read off bar code or by some other means, and may be stored in memory 348 of computer 346. The analyte concentration of the solution of interest then may be calculated from equation (3).

A special case of equation (3) occurs here [A]<<1/$K_A$, in which case [A] is approximately $f_b/K_A$. Accordingly, an alternate computation may be used.

Two two-well biosensors may be used to determine concentration. One biosensor would include $I_{MIN}$ and $I_{VAR-KNOWN}$ and the other biosensor would include $I_{MIN}$ and $I_{VAR-UNKNOWN}$. $I_{MAX}$ may be obtained from $I_{VAR-KNOWN}$ through equations (1) and (2). The two two-well biosensors may have greater value in large clinical labs that make many samples.

Data Fitting Function

A rate-based method may also be used. In such a method, the following formula may be used:

$$I_{(t)} = R_{ti} \frac{(e^{K*ti})}{K}(1 - e^{-Ki}) + I_o$$

wherein $I_{(t)}$, t) are intensity versus time data, $R_{ti}$ is the reaction rate at time ti, $I_o$ is intensity at time t equals 0, and K is the mass transport constant for a given waveguide, flow cell or reagent set (e.g. K may be approximately 0.06 Min.$^{-1}$).

Figure 10:
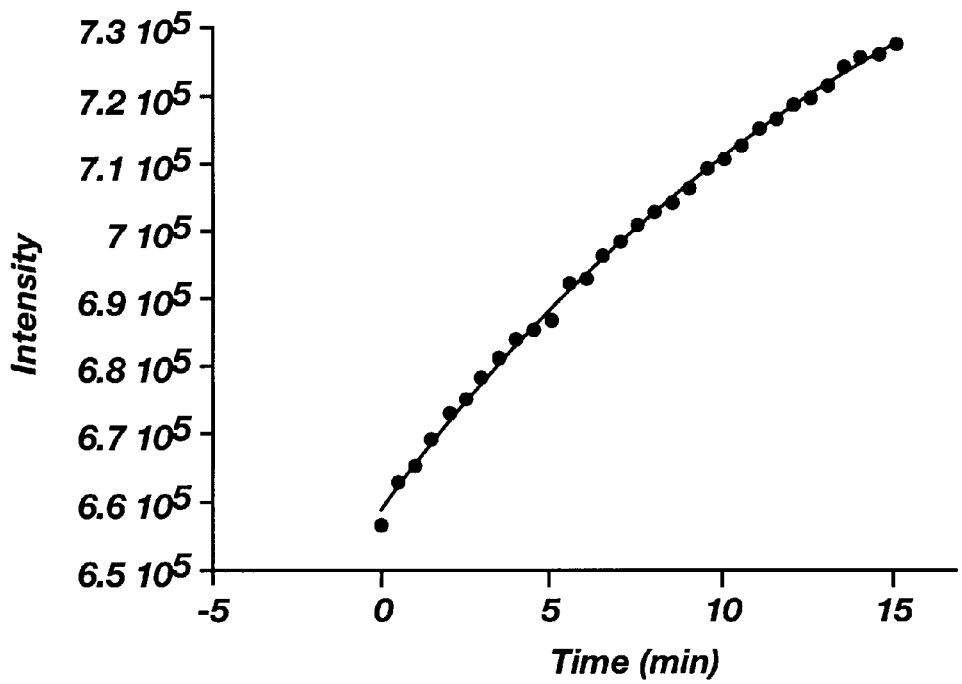
FIGS. 10 through 12 are graphs depicting various analyses of fit of experiments performed according to the invention.

In this regard, FIG. 10 is a graph plotting intensity versus time in minutes, and the resulting non-linear curve fit of an analysis of 30 nanograms ("ng") of a standard CKMB (Recombinant CKMB added by mass to stripped human plasma (Genzyme)] with an apparatus of the instant invention. In FIG. 10, $I_o$ has a value 6.5905e+05 (error 420.86), K has a value 0.059511 (error 0.0034), rate is 4467.5 (error 33.17) at 7.5 minutes, and R value of 0.99937.

Figure 11:
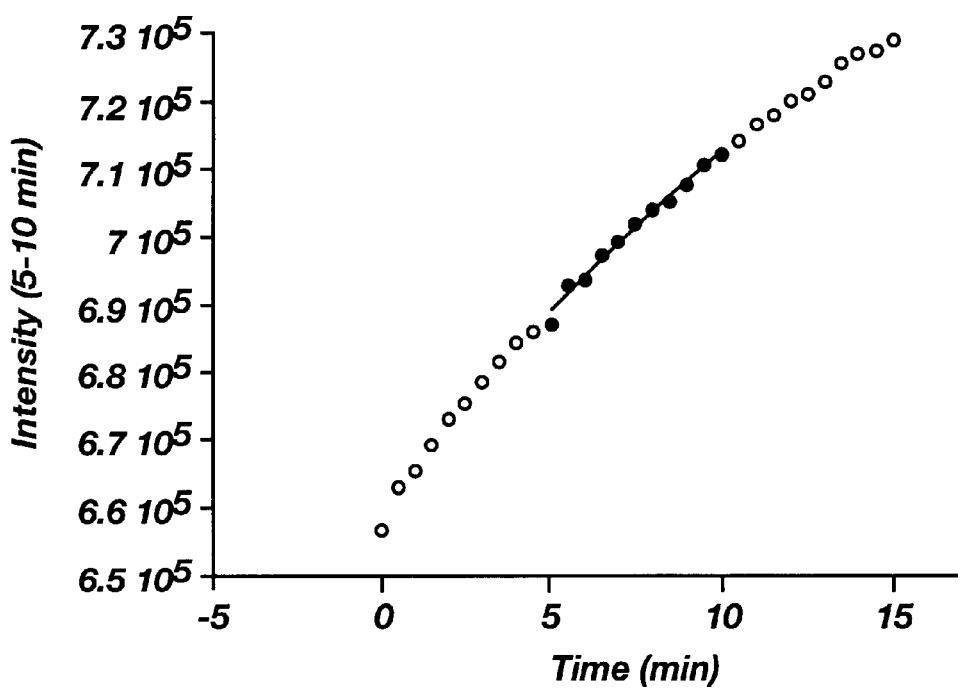

FIG. 11 is a graph plotting intensity versus time (in minutes) with a linear curve fit (showing linear regression) of an analysis of 30 ng of a standard CKMB [(Recombinant CKMB added by mass to stripped human plasma (Genzyme)] with an apparatus of the instant invention. For this graph (at t=7.5 min.), y=6.6688e+05+4509.3x m$^{-1}$, and R was 0.99197.

Figure 12:
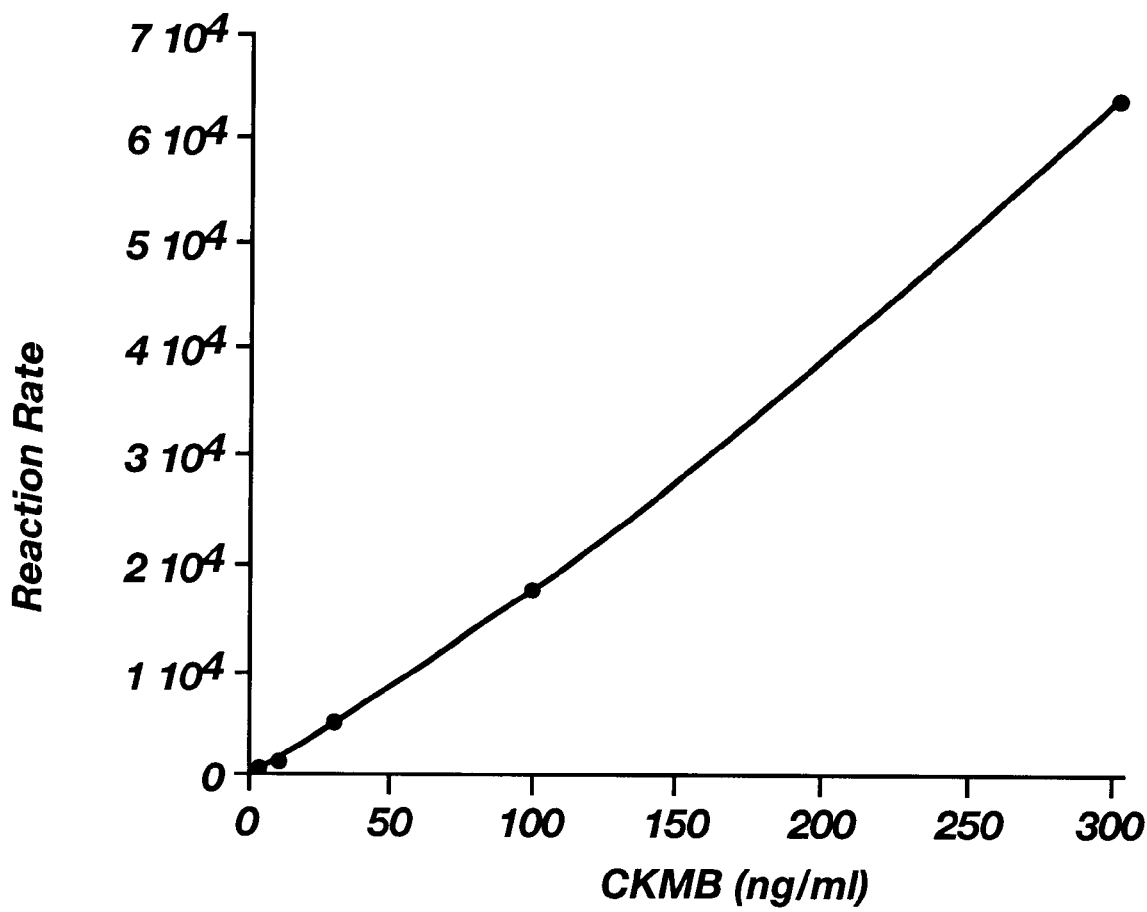
Figure 13A:
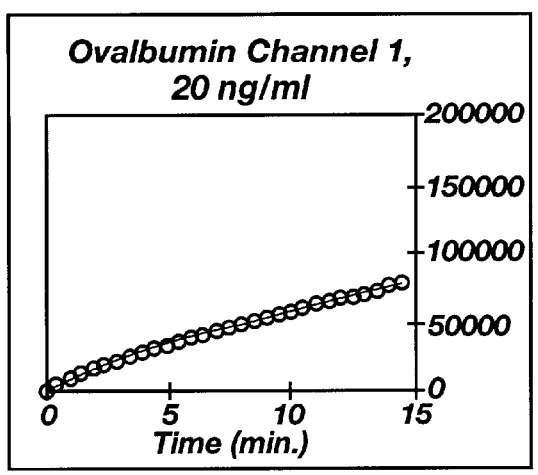
FIGS. 13 through 15 are graphs depicting results of various multi-analyte analysis experiments performed according to the invention.
Figure 13D:
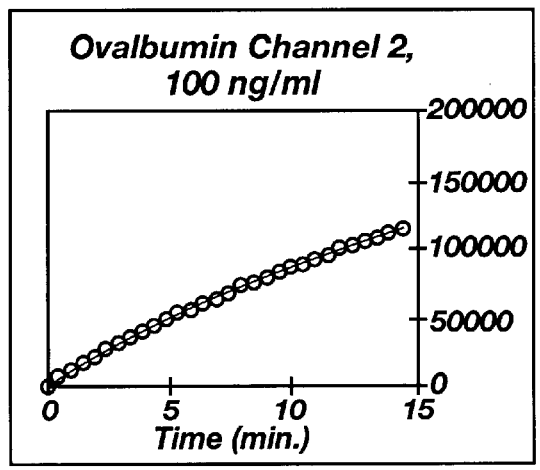
Figure 13B:
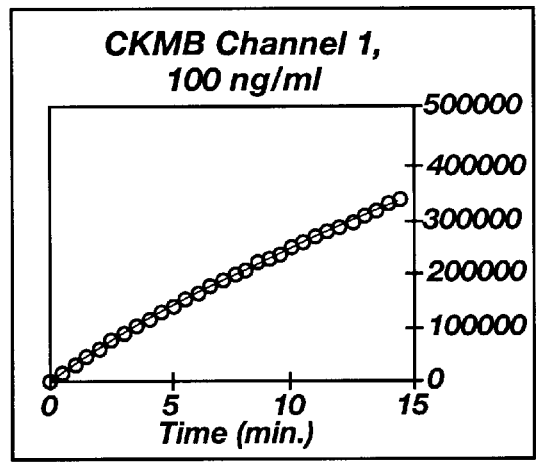
Figure 13E:
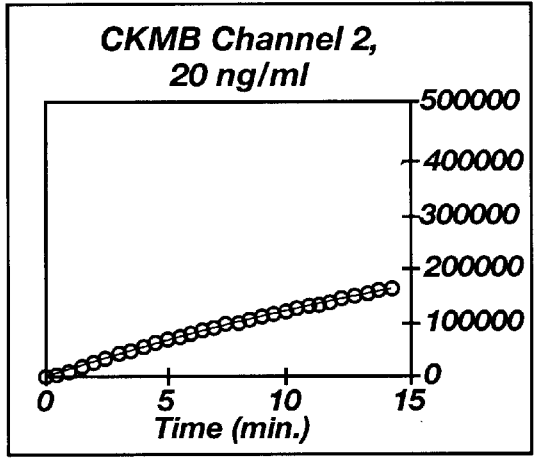
Figure 13C:
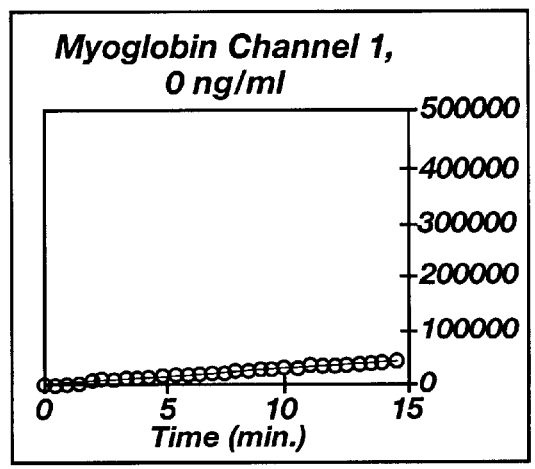
Figure 13F:
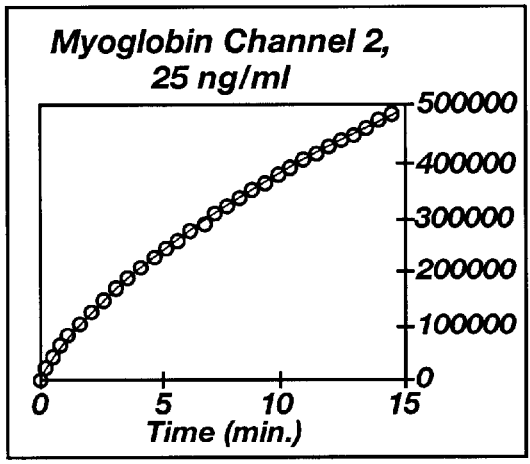
Figure 13G:
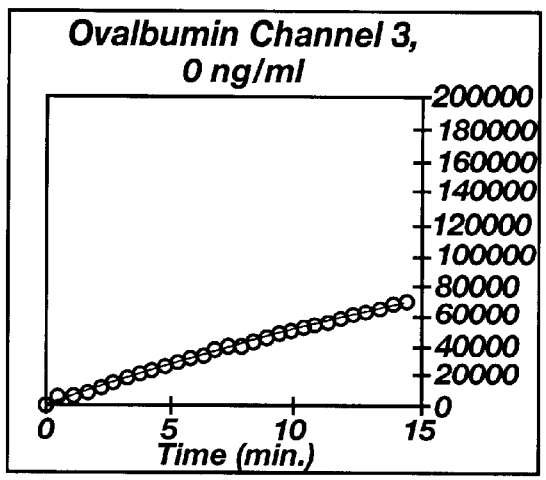
Figure 13J:
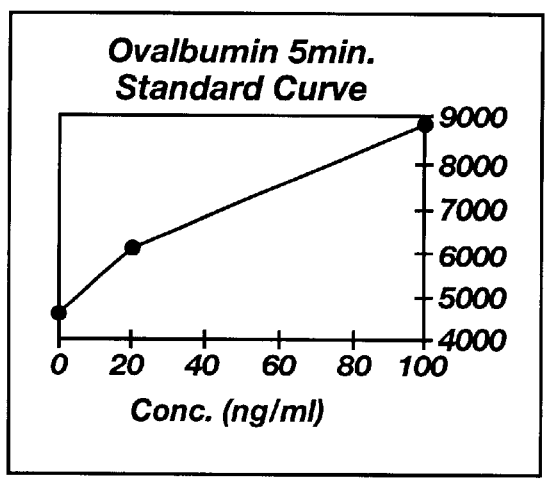
Figure 13H:
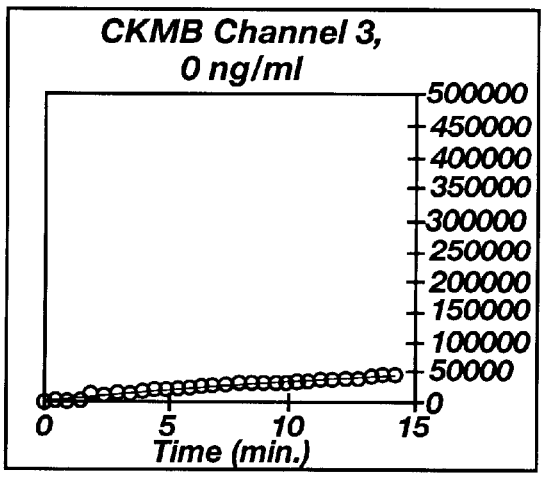
Figure 13K:
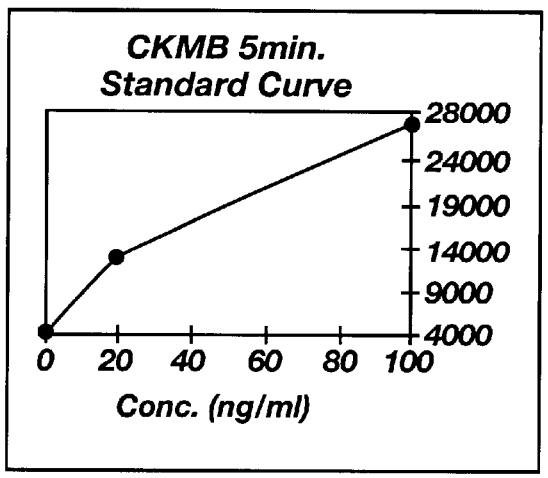
Figure 13I:
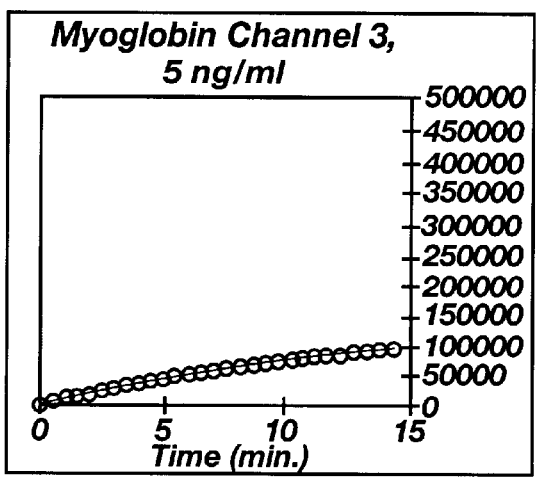
Figure 13L:
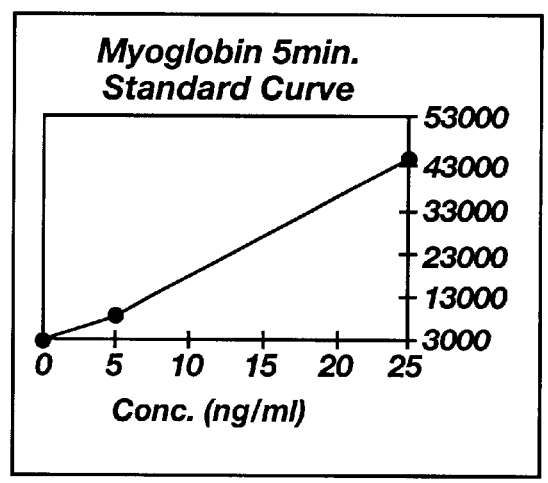
Figure 14A:
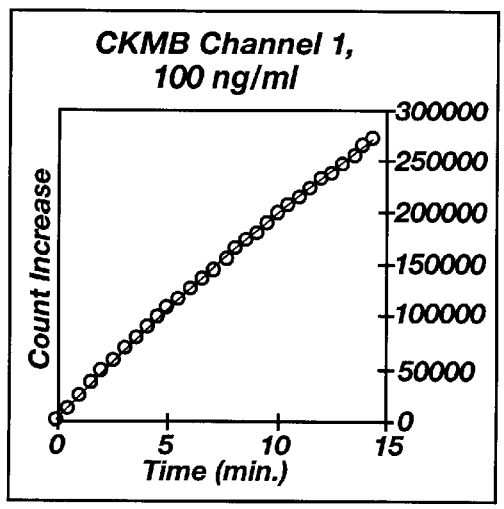
Figure 14D:
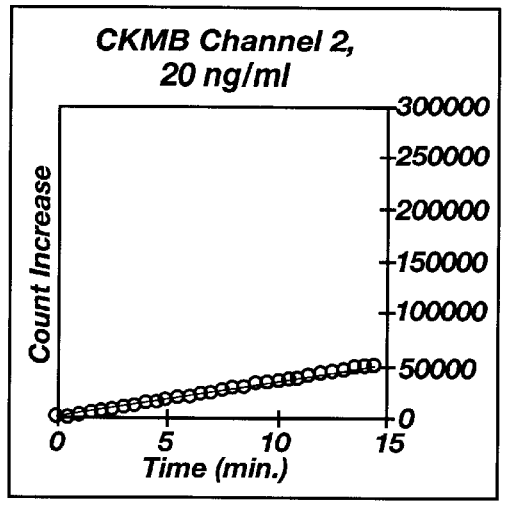
Figure 14B:
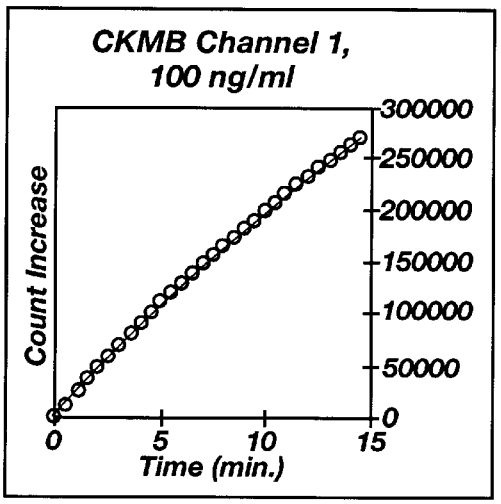
Figure 14E:
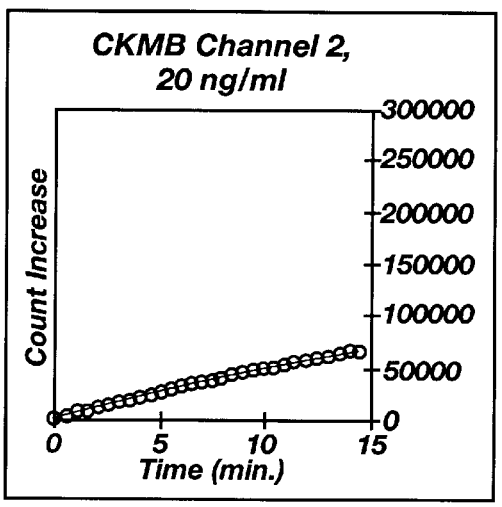
Figure 14C:
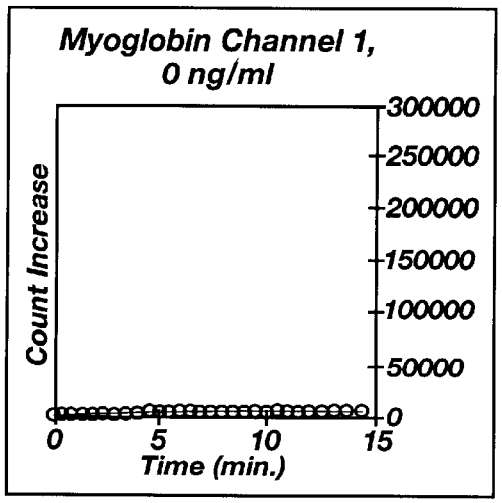
Figure 14F:
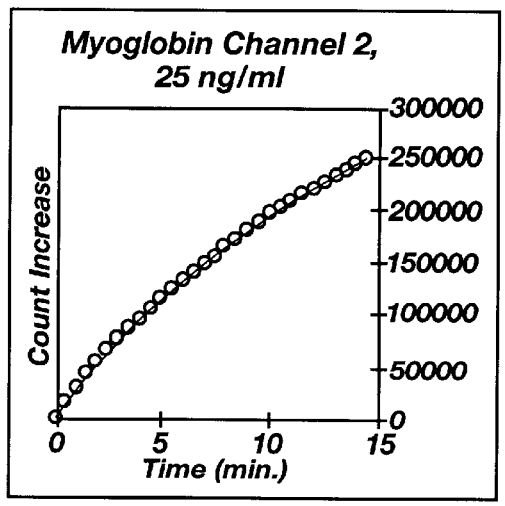
Figure 14G:
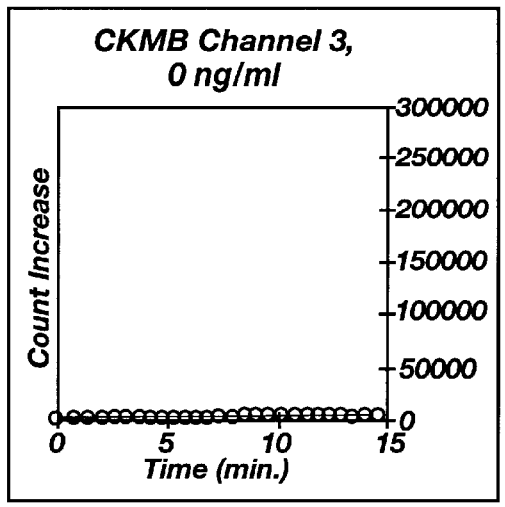
Figure 14J:
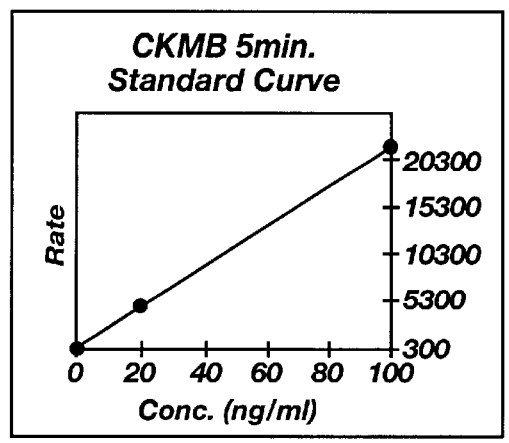
Figure 14H:
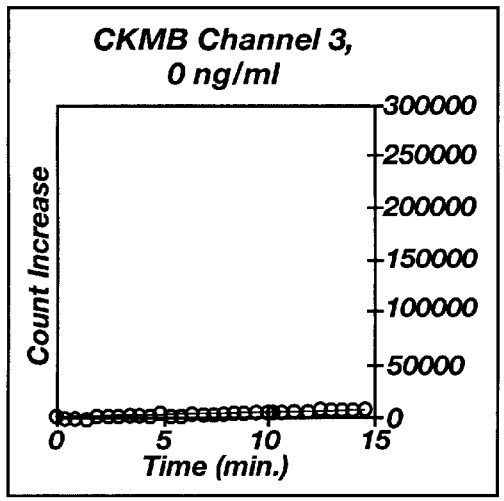
Figure 14K:
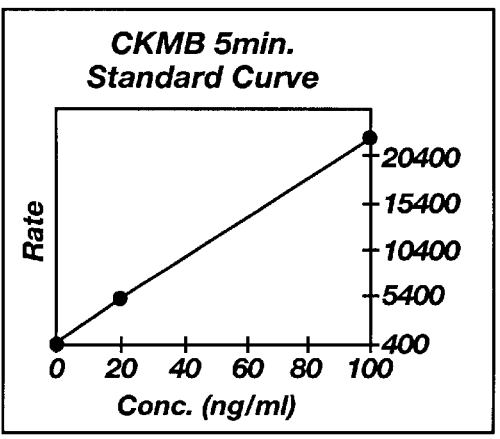
Figure 14I:
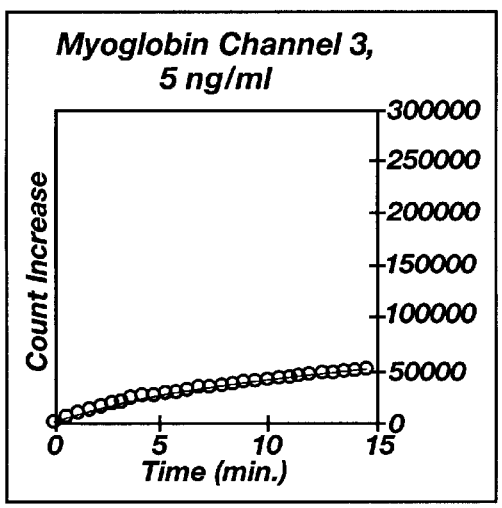
Figure 14L:
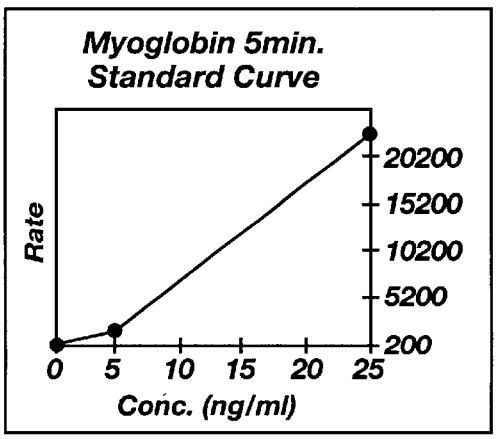
Figures 15A, 15B:
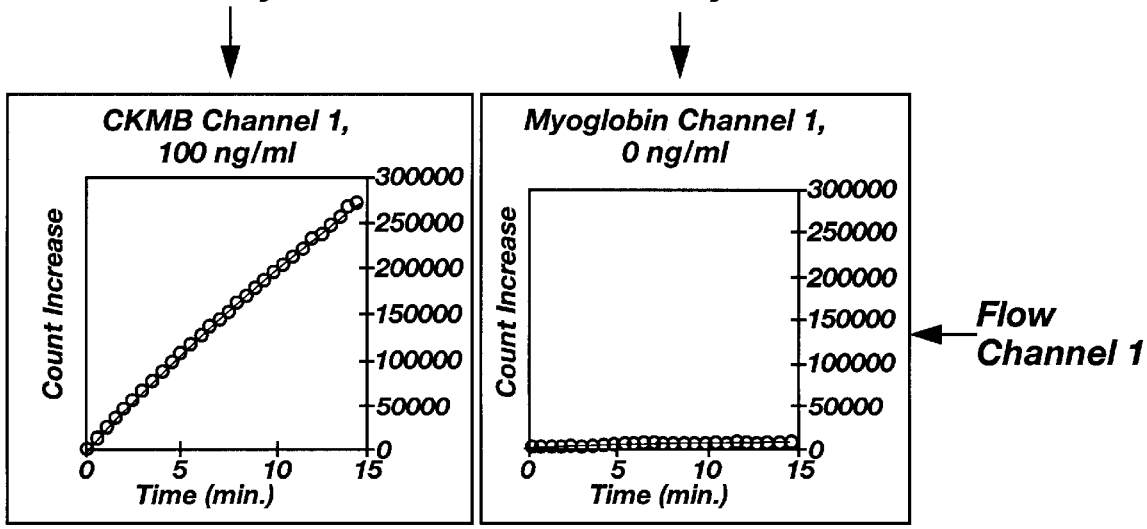
Figures 15C, 15D:
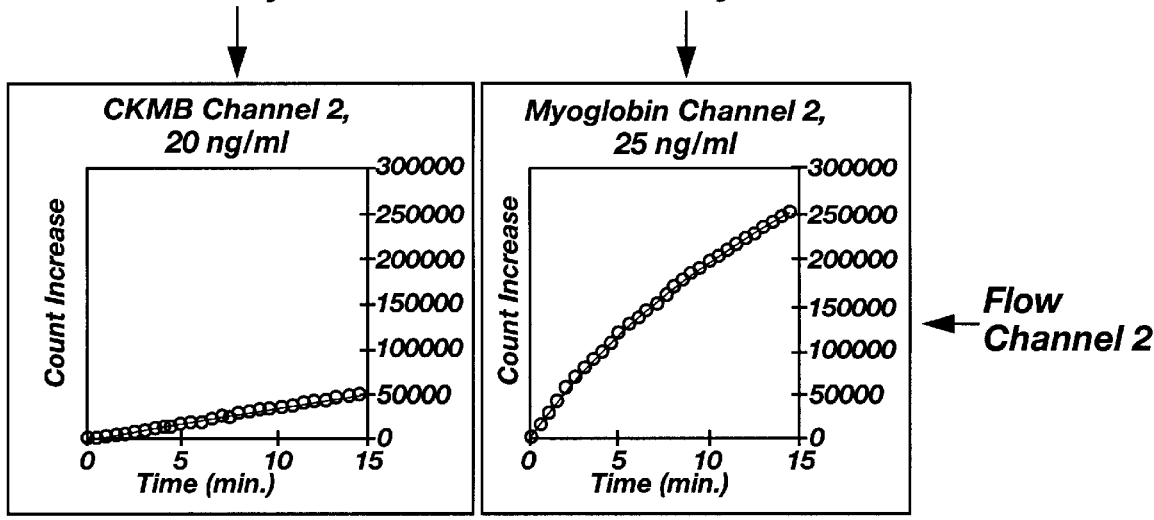
Figure 15E:
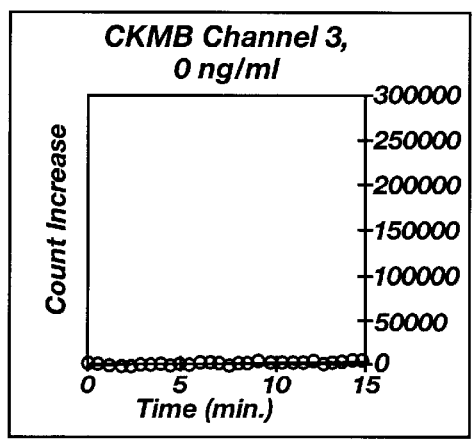
Figure 15F:
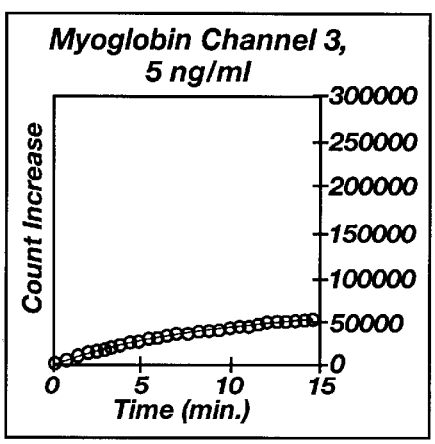
Figure 15G:
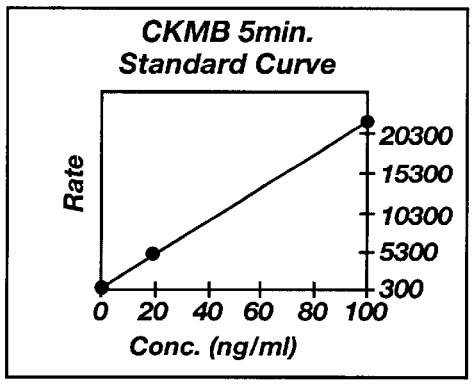
Figure 15H:
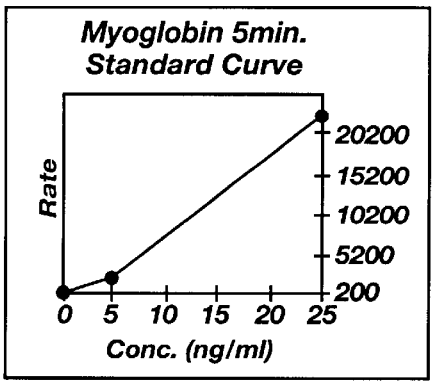

FIG. 12 is a graph plotting reaction rate versus CKMB concentration (ng/ml) detected. A standard curve was displayed having a quadratic curve fit:

(Rate=A+B*[CKMB]+C*[CKMB]$^2$ wherein A was 68.268, B was 162.45, C was 0.16778, and R was 0.99998.

Examples of the results of a multi-analyte assay conducted in accordance with the disclosure of the present invention are illustrated in FIGS. 13, 14, and 15. FIG. 13 illustrates a three analyte assay. Three samples were placed in a three channeled/welled biosensor consistent with the method described above. The three samples contained various known concentrations of Ovalbumin, CK-MB, and Myoglobin, the analytes of interest. More specifically, sample 1 contained 20 ng/ml of Ovalalbumin, 100 ng/ml of CK-ME, and 0 ng/ml of Myoglobin. Sample 2 contained 100 ng/ml of Ovalbumin, 20 ng/ml of CK-MB, and 25 ng/ml of Myoglobin. Sample 3 contained 0 ng/ml of Ovalbumin, 0 ng/ml of CK-MB, and 5 ng/ml of Myoglobin.

Each of the samples were placed in a respective channel (i.e., sample 1 in channel 1, sample 2 in channel 2, and sample 3 in channel 3) with an equal volume of tracer molecules (i.e., 200 microliters of sample and 200 microliters of tracer molecule solution). The tracer molecules used were as follows: a Cy5 labelled goat antiovalbumin antibody for detecting Ovalbumin, a Cy5 labelled BILL monoclonal anti-CK-BB antibody for detecting CK-MB, and a Cy5 labelled monoclonal antibody IGG from Genzyme, Inc. (one of the non-competing pair IGG$_1$ or IGG$_2$) for detecting Myoglobin. The channels/wells each had respective capture areas containing capture molecules specific for each of the analytes of interest (i.e., rabbit antiovalbumin for Ovalbumin, CONAN monoclonal anti-CK-MB antibody for CK-MB, and monoclonal antibody IGG (either IGG$_1$ or IGG$_2$—which ever is not being utilized as the tracer molecule) for Myoglobin). The intensity of the fluorescence for a given apparatus (Y-axis) for each of the capture areas over the time span of 15 minutes (X-axis) were plotted, as shown in FIG. 13. Thus, it can be seen that multiple analytes of interest can be detected and their concentrations determined using a single assay.

FIG. 14 illustrates a multi-analyte assay having two analytes of interest, CK-MB and Myoglobin. The assays were conducted in the manner described above. However, the channels/wells contained two capture areas for the CK-MB in order to determine whether variations occurred between capture areas. It can be seen from the graph of FIG. 14 that virtually no variations occurred. FIG. 15 illustrates another multi-analyte assay having two analytes of interest, CK-MB and Myoglobin.

Further each of FIGS. 13, 14, and 15 include standard curve graphs for each analyte of interest across the three channes/wells. The standard curves where generated by determining the slope of the line over the first five minutes for each assay concentration which where plotted against each concentration. Thus, the concentration of an analyte of interest having an unknown concentration can be determined from this curve.

F. Various Types of Light Sources

Light source 84 may be an argon laser capable of emitting light at center wavelengths of between about 488 nm and 514.5 nm (nanometers). In an alternate embodiment, light source 84 is a laser diode emitting at center wavelengths of 600 nm to about 900 nm. Depending on the requirements of the fluorescent tracer, light source 84 may also be embodied as any other laser or other high-intensity light source emitting a sufficient amount of light at an appropriate wavelength to excite the selected tracer.

It is desirable that the wavelength of light beam 184 entering waveguide 122 be significantly different from the wavelength of fluorescent light so that light beam 184 may be filtered out.

Although the illustrated embodiments have been describing in terms of top and bottom, the invention does not have to be constructed with components aligned with the direction of gravity.

It will further be recognized that various modifications and substitutions may be made to the apparatus and the biosensor as described herein, without departing from the concept and scope of the invention.

What is claimed is:

1. A method of simultaneously detecting light emanating from a plurality of discrete areas of a biosensor and passing through a waveguide, said method comprising:

simultaneously emanating light from a plurality of discrete areas of a biosensor;

segregating the light simultaneously emanating from each discrete area of said plurality of discrete areas of the biosensor from other light simultaneously emanating from other discrete areas of the plurality of discrete areas of the biosensor by concurrently channeling the light from each said discrete area;

directing the segregated light simultaneously emanating from each said discrete area of said plurality of discrete areas of the biosensor to a respective photodetector for each said discrete area of said plurality of discrete areas; and detecting the segregated light simultaneously emanating from each said discrete area of said plurality of discrete areas of the biosensor with said respective photodetector.

2. The method of claim 1, wherein the light simultaneously emanating from each said discrete area of said plurality of discrete areas of the biosensor is segregated from other light simultaneously emanating from other discrete areas of said plurality of discrete areas of the biosensor by means of a structure which defines an inlet opening therein and a channel associated with said inlet opening, said inlet opening being positioned adjacent each said discrete area of said plurality of discrete areas of the biosensor, whereby light emanating from each said discrete area of said plurality of discrete areas of the biosensor passes through said inlet opening and thereafter through said channel to said respective photodetector.

3. The method of claim 1, wherein the segregated light emanating from each said discrete area of said plurality of discrete areas of the biosensor is directed to the respective photodetector by at least one lens associated optically and interposed between each said discrete area of said plurality of discrete areas of the biosensor and the respective photodetector.

4. The method of claim 2, wherein the segregated light emanating from each said discrete area of said plurality of discrete areas of the biosensor is directed to the respective photodetector by at least one mirror.

5. The method of claim 4, wherein the mirror is a parabolic mirror.

6. The method of claim 1, wherein the photodetector is a CCD camera.

7. The method of claim 6, wherein the CCD camera is coupled to a grating spectrograph for spectral analysis of the detected light, and further including the step of detecting a total collected fluorescence of a sample.

8. An apparatus for detecting fluorescent light emanating from a plurality of discrete areas of a biosensor, said apparatus comprising:
   a light source for simultaneous emanation of fluorescent light through a plurality of discrete areas of a biosensor;
   a grate, optically associated with said plurality of discrete areas of the biosensor and said light source, for concurrently segregating fluorescent light simultaneously emanating from each discrete area of said plurality of discrete areas of the biosensor from fluorescent light simultaneously emanating from other discrete areas of said plurality of discrete areas of the biosensor; and
   a structure for focusing the segregated fluorescent light onto a respective photodetector.

9. The apparatus of claim 8, wherein the structure for focusing the segregated fluorescent light is selected from the group of a lens, mirror, fiber optic cable, and combinations thereof.

10. A method for determining analyte concentration, said method comprising:
    activating a light source to simultaneously emanate fluorescent light through a plurality of discrete areas of a biosensor, with
        a grate, optically associated with said plurality of discrete areas of the biosensor and said light source, for concurrently segregating fluorescent light simultaneously emanating from each discrete area of said plurality of discrete areas of the biosensor from fluorescent light simultaneously emanating from other discrete areas of said plurality of discrete areas of the biosensor; and
        a structure for focusing the segregated fluorescent light onto a respective photodetector; and detecting fluorescent light emanating from a plurality of discrete areas of a biosensor.

11. The method of claim 10 further comprising focusing the segregated fluorescent light is selected from the group of a lens, mirror, fiber optic cable, and combinations thereof.

12. A method of simultaneously determining the presence of a plurality of analytes in a sample, said method comprising:
    providing a biosensor having a waveguide and a plurality of patches disposed within a well defined in said waveguide, a first patch of said plurality of patches having a first type of capture molecule associated therewith, and a second patch of said plurality of patches having a second type of capture molecule associated therewith;
    introducing a sample believed to contain a plurality of analytes into said well;
    introducing at least one type of tracer molecule into said well, said tracer molecule comprising a fluorescent label bonded to a molecule that binds with either one of said first type and said second type of capture molecules or to at least one analyte of said plurality of analytes;
    directing light through said waveguide, said light having a wave length which will excite said fluorescent label;
    segregating fluorescent light emanating from said first patch from light simultaneously emanating from said second patch and light simultaneously emanating from a remainder of said biosensor by channeling said fluorescent light emanating from said first patch;
    segregating fluorescent light emanating from said second patch from light simultaneously emanating from said first patch and light simultaneously emanating from said remainder of said biosensor by channeling said fluorescent light emanating from said second patch;
    detecting said segregated fluorescent light emanating from said first patch with a first photodetector;
    detecting said segregated fluorescent light emanating from said second patch with a second photodetector;
    analyzing said segregated fluorescent light emanating from said first patch to determine a presence of a first analyte; and
    analyzing said segregated fluorescent light emanating from said second patch to determine a presence of a second analyte.

13. The method of claim 12, wherein each said first and second patches of said plurality of patches is associated with a respective unique capture molecule.

14. The method of claim 12, further including the step of introducing a plurality of types of tracer molecules into said well, wherein each said type of tracer molecule of said plurality of types of tracer molecules has an affinity for a respective type of analyte being investigated.

15. The method of claim 12, wherein said sample and said plurality of types of tracer molecules are introduced simultaneously into said well.

16. A method of simultaneously determining the individual concentration of several analytes in a sample, said method comprising:
    providing a biosensor having a waveguide which defines a first well and a second well and a plurality of patches disposed within said first and second wells, each said first and second wells containing a first patch of said plurality of patches having a first type of capture molecule associated therewith and a second patch of said plurality of patches having a second type of capture molecule associated therewith;
    introducing a sample believed to contain a first analyte and a second analyte into said first well;
    introducing a first liquid containing first known quantities of said first analyte and said second analyte into said second well;
    introducing at least one type of tracer molecule into said first well and into said second well, said tracer molecule comprising a fluorescent label bonded to a molecule that binds with either one of said first and second types of capture molecules or at least one of said first and second analytes;

directing light through said waveguide, said light having a wave length which will excite said fluorescent label;

segregating fluorescent light emanating from said first patch in said first well from fluorescent light simultaneously emanating from said first patch in said second well, from fluorescent light simultaneously emanating from said second patches in said first well and said second well, and from fluorescent light simultaneously emanating from a remainder of said biosensor by channeling said fluorescent light emanating from said first patch in said first well;

segregating fluorescent light emanating from said first patch in said second well from fluorescent light simultaneously emanating from said first patch in said first well, from fluorescent light simultaneously emanating from said second patches in said first well and said second well, and from fluorescent light simultaneously emanating from a remainder of said biosensor by channeling said fluorescent light emanating from said first patch in said second well;

segregating fluorescent light emanating from said second patch in said first well from fluorescent light simultaneously emanating from said second patch in said second well, from fluorescent light simultaneously emanating from said first patches in said first well and said second well, and from fluorescent light simultaneously emanating from a remainder of said biosensor by channeling said fluorescent light emanating from said second patch in said first well;

segregating fluorescent light emanating from said second patch in said second well from fluorescent light simultaneously emanating from said second patch in said first well, from fluorescent light simultaneously emanating from said first patches in said first well, and said second well, and from fluorescent light simultaneously emanating from a remainder of said biosensor by channeling said fluorescent light emanating from said second patch in said second well;

detecting said segregated fluorescent light emanating from said first patch in said first well with a first photodetector;

detecting said segregated fluorescent light emanating from said first patch in said second well with a second photodetector;

detecting said segregated fluorescent light emanating from said second patch in said first well with a third photodetector;

detecting said segregated fluorescent light emanating from said second patch in said second well with a fourth photodetector;

analyzing said segregated fluorescent light emanating from said first patch in said first well detected by said first photodetector in view of said segregated fluorescent light simultaneously emanating from said first patch in said second well detected by said second photodetector to determine a concentration of said first analyte in said sample;

analyzing said segregated fluorescent light emanating from said second patch in said first well detected by said third photodetector in view of said segregated fluorescent light simultaneously emanating from said second patch in said second well detected by said fourth photodetector to determine a concentration of said second analyte in said sample.

17. The method of claim 16, wherein said first liquid contains no said first analytes and no said second analytes.

18. The method of claim 16, wherein said biosensor defines a third well and a plurality of patches disposed within said third well, said third well containing a first patch of said plurality of patches having said first type of capture molecule associated therewith and a second patch of said plurality of patches having said second type capture molecule associate therewith, said method further comprising the steps of:

introducing a second liquid having second known quantities of said first analyte and said second analyte into said third well;

introducing said at least one type of tracer molecule into said third well;

segregating fluorescent light emanating from said first patch in said third well from fluorescent light simultaneously emanating from said second patch in said third well, from fluorescent light emanating from said first patches in said first well and said second well, from light simultaneously emanating from said second patch in said second well, and from fluorescent light simultaneously emanating from the remainder of said biosensor by channeling said fluorescent light emanating from said first patch in said third well;

segregating fluorescent light emanating from said second patch in said third well from fluorescent light simultaneously emanating from said first patch in said third well, from fluorescent light simultaneously emanating from said first patches in said first well and said second well, from light simultaneously emanating from said second patches in said first well and said second well and a remaining portion of said biosensor by channeling said fluorescent light emanating from said second patch in said third well;

detecting said segregated fluorescent light emanating from said first patch in said third well with a fifth photodetector;

detecting said segregated fluorescent light emanating from said second patch in said third well with a sixth photodetector;

analyzing said segregated fluorescent light emanating from said first patch in said first well detected by said first photodetector in view of said light simultaneously emanating from said first patch in said second well detected by said second photodetector and said segregated fluorescent light simultaneously emanating from said first patch in said third well detected by said fifth photodetector to determine a concentration of said first analyte in said sample; and analyzing said segregated fluorescent light emanating from said second patch in said first well detected by said third photodetector in view of said segregated fluorescent light simultaneously emanating from said second patch in said second well detected by said fourth photodetector and said fluorescent light simultaneously emanating from said second patch in said third well detected by said sixth photodetector to determine a concentration of said second analyte in said sample.

19. The method of claim 18, wherein said at least one type of tracer molecule is introduced into said third well simultaneously with said second liquid.

20. The method of claim 16, 17, 18 or 19, wherein said at least one type of tracer molecule is introduced into said well simultaneously with said sample.

21. The method of claim 16, 17, 18 or 19, wherein said at least one type of tracer molecule is introduced into said second well simultaneously with said first liquid.

22. The method of claim 16, 17, 18 or 19, wherein said at least one type of tracer molecule is introduced into said third well simultaneously with said second liquid.

23. The method of claim 20, wherein said at least one type of tracer molecule is introduced into said third well simultaneously with said second liquid.

* * * * *